US010266566B2

(12) United States Patent
Menegatti et al.

(10) Patent No.: US 10,266,566 B2
(45) Date of Patent: Apr. 23, 2019

(54) PROTEASE-RESISTANT PEPTIDE LIGANDS

(71) Applicant: North Carolina State University, Raleigh, NC (US)

(72) Inventors: Stefano Menegatti, Raleigh, NC (US); Benjamin G. Bobay, Raleigh, NC (US); Ruben G. Carbonell, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 319 days.

(21) Appl. No.: 14/904,715

(22) PCT Filed: Jul. 15, 2014

(86) PCT No.: PCT/US2014/046660
§ 371 (c)(1),
(2) Date: Jan. 13, 2016

(87) PCT Pub. No.: WO2015/009701
PCT Pub. Date: Jan. 22, 2015

(65) Prior Publication Data

US 2016/0159859 A1 Jun. 9, 2016

Related U.S. Application Data

(60) Provisional application No. 61/846,326, filed on Jul. 15, 2013.

(51) Int. Cl.

| | |
|---|---|
| ***C07K 1/22*** | (2006.01) |
| ***C07K 7/06*** | (2006.01) |
| ***C07K 7/08*** | (2006.01) |
| ***C07K 16/06*** | (2006.01) |

(52) U.S. Cl.
CPC .................. *C07K 7/06* (2013.01); *C07K 1/22* (2013.01); *C07K 7/08* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 7,807,799 | B2 | 10/2010 | Fahrner et al. |
| 2006/0153834 | A1 | 7/2006 | Carbonell et al. |
| 2006/0160064 | A1 | 7/2006 | Carbonell |
| 2012/0021975 | A1 | 1/2012 | Hoffmann et al. |
| 2013/0165539 | A1 | 1/2013 | Carbonell et al. |

FOREIGN PATENT DOCUMENTS

| | | |
|---|---|---|
| KR | 100953917 | 4/2010 |
| WO | 2010/089116 | 8/2010 |

OTHER PUBLICATIONS (https://www.lifetein.com/Peptide-Synthesis-D-Amino-Acid.html, accessed Sep. 18, 2017).*

Gentilucci et al. ("Chemical Modifications Designed to improve Peptide Stability: Incorporation of Non-natural amino acids, Pseudo-peptide Bonds and Cyclization" Current Pharmaceutical Design, 2010, 16 (3185-3203).*

Qu ("Synthesis of Novel Amino Acids and Use of Peptides & Peptidomimetics Containing Unnatural Amino Acids for the Development of Selective Melanocortin Peptide Antagonists and for the Study of Melanocortin Receptor Signaling" Dissertation in the Graduate College of University of Arizona; Nov. 19, 2007).*

Andrusier, N. et al., "Principles of flexible protein-protein docking," Proteins (2008) 73:271-289.

Appel, W., "Chymotrypsin: molecular and catalytic properties," Clin. Biochem. (1986) 19:317-322.

Artigas, J.M. et al., "Serum trypsin levels in acute pancreatic and non-pancreatic abdominal conditions," Postgrad. Med. J. (1981) 57:219-222.

Backer, M.P. et al., "Large-scale production of monoclonal antibodies in suspension culture," Biotechnol. Bioeng. (1988) 32:993-1000.

Bischoff, R. et al., "Deamidation of asparagine and glutamine residues in proteins and peptides: structural determinants and analytical methodology," J. Chromatogr. B Biomed. Appl. (1994) 662:261-278.

Brekke, O.H. et al., "Therapeutic antibodies for human diseases at the dawn of the twenty-first century," Nat. Rev. Drug Discovery (2003) 2:52-62.

D'Agostino et al., "Affinity purification of IgG monoclonal antibodies using the D-PAM synthetic ligand: chromatographic comparison with protein A and thermodynamic investigation of the D-PAM/IgG interaction," J. Immunol. Methods (2008) 333:126-138.

De Vries, S.J. et al., "HADDOCK versus HADDOCK: new features and performance of HADDOCK2.0 on the CAPRI targets," Proteins: Struc. Funct. 7 Bioinformatic (2007) 69:726-733.

Dominguez, C. et al., "HADDOCK: a protein-protein docking approach based on biochemical or biophysical information," J. Am. Chem. Soc. (2003) 125:1731-1737.

ElBakri, A. et al., "The state of antibody therapy," Hum. Immunol. (2010) 71:1243-1250.

Eldridge et al., "An in vitro selection strategy for conferring protease resistance to ligand binding peptides," protein Eng. Des. Sel. (2009) 22:691-698.

Follman, D.K. et al., "Factorial screening of antibody purification processes using three chromatography steps without protein A," J. Chromatogr. A (2004) 1024:79-85.

Gagnon, P., "Technology trends in antibody purification," J. Chromatogr. A (2012) 1221:57-70.

Galati et al., "Increased resistance of peptides to serum proteases by modification of their amino groups," Z. Naturforsch C. (2003) 58c:558-561.

(Continued)

*Primary Examiner* — Jennifer Pitrak McDonald
*Assistant Examiner* — Tara L Martinez
(74) *Attorney, Agent, or Firm* — Michael Best & Friedrich LLP

(57) ABSTRACT

This invention relates generally to the discovery of novel protease-resistant peptide ligands and uses thereof. Specifically, the present invention provides a protease-resistant peptide with three to twenty amino acids capable of binding a biological and comprising one or more basic amino acid(s) and I or aromatic amino acids, wherein one or more of the amino acids is substituted with a non-naturally occurring amino acid analog.

12 Claims, 4 Drawing Sheets

Figure 1:
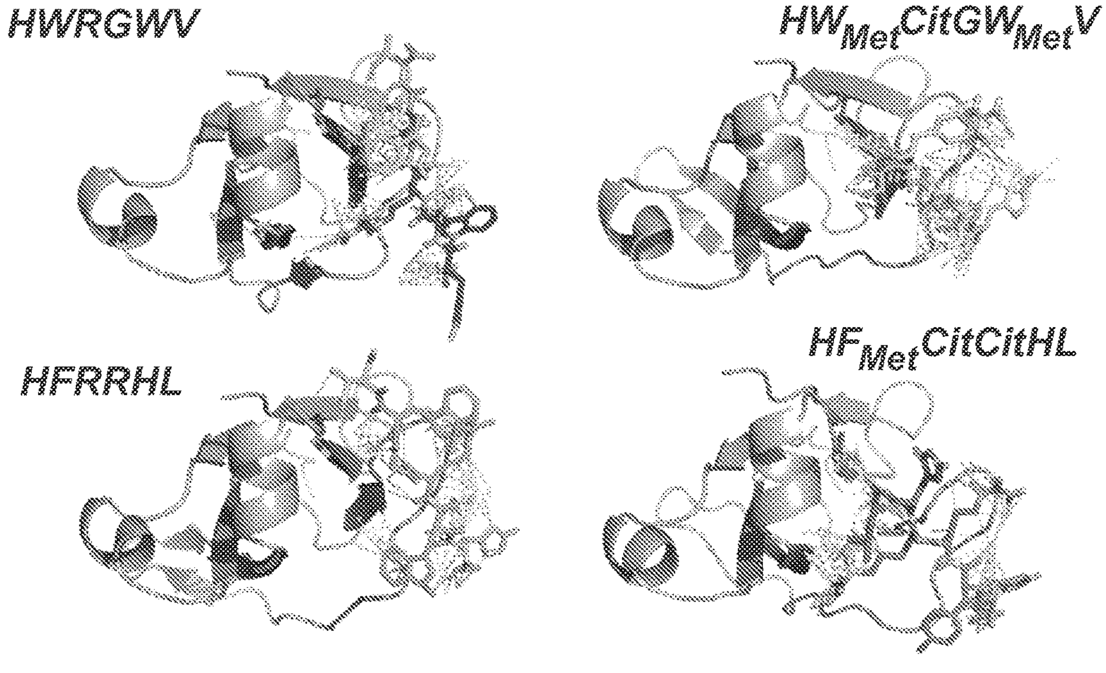

Specification includes a Sequence Listing.

(56) References Cited

OTHER PUBLICATIONS

Grodzki, A.C. et al., "Antibody purification: affinity chromatography—protein a and protein G sepharose," Methods Mol. Biol. (2010) 588:33-41.
Hahn, R. et al., "Comparison of protein a affinity sorbents," J. Chromatogr. B. Analyt. Technol. Biomed. Life Sci. (2003) 790:35-51.
Hober, S. et al., "Protein A chromatography for antibody purification," J. Chromatogr. B. (2007) 848:40-47.
Hubbard, S.J. et al., "Molecular Recognition. Conformational analysis of limited proteolytic sites and serine proteinase protein inhibitors," J. Mol. Biol. (1991) 220:507-530.
International Search Report and Written Opinion for Application No. PCT/US2014/046660 dated Dec. 24, 2014 (9 pages).
Jeschke, U. et al., "Development of monoclonal and polyclonal antibodies and an ELISA for the determination of glycodelin in human serum, amniotic fluid and cystic fluid of benign and malignant ovarian tumors," Anticancer Res. (2005) 25:1581-1590.
Joshi, A.B. et al., "The relative rates of glutamine and asparagine deamidation in glucagon fragment 22-29 under acidic conditions," J. Pharm. Sci. (2002) 91:2331-2344.
Kawakami et al., "Messenger RNA-programmed incorporation of multiple N-methyl-amino acids into linear and cyclic peptides," Chem. Biol. (2008) 15:32-42.
Kazatchkine, M.D. et al., "Immunomodulation of autoimmune and inflammatory diseases with intravenous immune globulin," N. Eng. J. Med. (2001) 345:747-755.
Kish, W.S. et al., "Peptide-based affinity adsorbents with high binding capacity for the purification of monoclonal antibodies," Ind. Eng. Chem. Res. (2012) 8800-8811.
Lefkowitz, R.B. et al., "An electrophoretic method for the detection of chymotrypsin and trypsin activity directly in whole blood," Electrophoresis (2010) 31:403-410.
Liu, S. et al., "A physical reference state unifies the structure-derived potential of mean force for protein folding and binding," Proteins: Structure, Function and Bioinformatics (2004) 56:93-101.
Liu, Z. et al., "Purification of human imunoglobulins A, G and M from Cohn fraction II/III by small peptide affinity chromatography," J. Chromatogr. A (2012) 1262:169-179.
Lonberg, N., "Human antibodies from transgenic animals," Nat. Biotechnol. (2005) 23:1117-1125.
Maschiach, E. et al., "FireDock: a web server for fast interaction refinement in molcular docking," Nucl. Acids Res. (2008) 36:W229-W232.
Menegatti, S. et al., "Alkaline-stable peptide ligand affinity adsorbents for the purification of biomolecules," J. Chromatogr. A (2012) 1245:55-64.
Menegatti, S. et al., "Purification of polyclonal antibodies from Cohn fraction II + III, skim milk, and whey by affinity chromatography using a hexamer peptide ligand," J. Pept. Sci. (2012) 35:3139-3148.
Naik, A.D. et al., "Performance of hexamer peptide ligands for affinity purification of immunoglobulin G from commercial cell culture media," J. Chromatogr. A (2011) 1218:1691-1700.
Naik, A.D. et al., "Process for purification of monoclonal antibody expressed in transgenic Lemna plant extract using dextran-coated charcoal and hemmer peptide affinity resin," J. Chromatogr. A (2012) 1260:61-66.

Newcombe, C. et al., "Antibody production: polyclonal-derived biotherapeutics," J. Chromatogr. B. (2007) 848:2-7.
Nygren, P.A. et al., "Analysis and use of the semm albumin binding domains of streptococcal protein G," J. Mol. Recognit. (1988) 1:69-74.
Olsen, J.V. et al., "Trypsin cleaves exclusively C-terminal to arginine and lysine residues," Mol. Cell. Proteomics (2004) 3:608-614.
Page, M. et al.,"Hybridoma production," in the Protein Protocols Handbook, Humana Press, J.M. Walker, editor (1996) p. 733-735.
Sauer-Eriksson, A.E. et al., "Crystal structure of the C2 fragment of streptococcal protein G in complex with the Fc domain of human IgG," Structure (1995) 3:265-278.
Schey, K.L. et al., "Identification of peptide oxidation by tandem mass spectrometry," Acc. Chem. Res. (2000) 33:299-306.
Simat, T.J. et al., "Oxidation of free tryptophan and tryptophan residues in peptides and proteins," J. Agric. Food Chem. (1998) 46:490-498.
Stave, J. W., "Detection of new or modified proteins in novel foods derived from GMO—future needs," Food Control (1999) 10:367-374.
Verdoliva et al., "Affnity purification of polyclonal antibodies using a new all-D synthetic peptide ligand: comparison with protein A and protein G," J. Immunol. Methods (2002) 271:77-88.
Vijayalakshmi Ayyar, B. et al., "Affinity chromatography as a tool for antibody purification," Methods (2012).
Wang, R. et al., "Comparative evaluation of 11 scoring functions for molecular docking," J. Med. Chem. (2003) 46:2287-2303.
Wang, R. et al., "Further development and validation of empirical scoring functions for structure-based binding affinity prediction," J. Comput. Aided Mol. Des. (2002) 16:11-26.
Weinstock et al., "Protease-resistant peptide design-empowering nature's fragile warriors against HIV," Biopolymers (2012) 98:431-442.
Yang, H. et al., "Hexamer peptide affinity resins that bind the Fc region of human immunoglobulin G," J. Pept. Res. (2005) 66 Suppl:120-137.
Yang, H. et al., "Purification of human immunoglobulin G via Fc-specific small peptide ligand affinity chromatography," J. Chromatogr. A (2009) A1216:910-918.
Yang, H.G. et al., "Binding site on human immunoglobulin G for the affinity ligand HWRGWV," J. Mol. Recognit. (2010) 23:271-292.
Zhang, C., "Hybridoma technology for the generation of monoclonal antibodies," in G. Proetzel et al. editors, Antibody Methods and Protocols, Humana press (2012) p. 117-136.
Zola, H., "Monoclonal antibodies: therapeutic uses," Encyclopedia of Life Sciences (2005) 1-8.
Australian Patent Office Examination Report No. 1 for Application No. 2014290229 dated Jan. 19, 2017 (4 pages).
New Zealand Patent Office First Examination Report for Application No. 716440 dated Nov. 7, 2016 (4 pages).
New Zealand Patent Office Further Examination Report for Application No. 716440 dated Mar. 10, 2017 (4 pages).
European Extended Search Report for Application No. 14826202.5 dated Jun. 8, 2017 (13 pages).
Subtelny et al., "Ribosomal Synthesis of N-Methyl Peptides," Journal of the American Chemical Society, 2008, vol. 130, No. 19, pp. 6131-6139.
Menegatti, "Design, Selection, and Development of Novel Peptide Ligands for Bioseparations and Diagnostics," Dissertation retreived from <https://repository.lib.ncsu.edu/handle/1840.16/8390> Mar. 26, 2013.

* cited by examiner

HWRGWV = SEQ ID NO:1

Ac-HWRGWV = SEQ ID NO:9

$HW_{Met}CitGW_{Met}V$ = SEQ ID NO:4

Ac-$HW_{Met}CitGW_{Met}V$ = SEQ ID NO:22

PROTEASE-RESISTANT PEPTIDE LIGANDS

CROSS-REFERENCE TO RELATED APPLICATIONS

This patent application is a national stage filing under 35 U.S.C. 371 of International Application No. PCT/US2014/046660, filed Jul. 15, 2014, which claims priority benefits to U.S. Provisional Patent Application No. 61/846,326, filed Jul. 15, 2013. These applications are incorporated herein by reference in their entireties.

1. FIELD OF THE INVENTION

This invention relates generally to the discovery of novel protease-resistant peptide ligands.

2. BACKGROUND OF THE INVENTION

1. Introduction

The purification of immunoglobulin from mammalian sera for therapeutic and research applications is an issue of considerable industrial, medical, and economical value. Polyclonal antibody-based therapeutics exhibit polyvalent interactions against multiple epitopes and targets and are therefore best suited for the prevention or treatment of some diseases. Plasma-derived polyclonal intravenous immunoglobulin (IVIG) preparations have been successfully applied to the prophylactic prevention of infectious diseases in immunodeficient patients and find increasing use against autoimmune and inflammatory problems. To date, IVIG is the major plasma product on the global blood product market, with a steadily increasing annual consumption. Polyclonal antibodies derived from animal plasma are also currently employed in research for producing immunoassays and to design therapeutic and diagnostic tools.

Affinity purification of polyclonal antibodies from mammalian sera is currently mostly based upon the use of protein ligands, such as Protein A and Protein G. These protein ligands, however, suffer from several drawbacks, such as 1) high cost ($15,000-20,000 per liter of adsorbent), 2) low chemical and biochemical stability, 3) immunogenicity, with the consequent risks associated to the leaching of ligand fragments in the product mainstream, and 4) harsh elution conditions, due to the high binding affinity, which threatens the bioactivity of the eluted protein. Further, Protein A does not bind human IgG3 and several animal immunoglobulins. Protein G, while binding all human IgG subclasses, shows also considerable binding of albumin, which is a major protein in human and animal plasma and its fractions.

To overcome these issues, synthetic ligands based on peptides, amino acids, triazine scaffolds and thiophillic compounds have been suggested for purification of antibodies. Our research group has identified three hexapeptide ligands, HWRGWV, HYFKFD and HFRRHL (SEQ ID NOS:1-3), which bind IgG through the Fc portion, thus mimicking the binding mechanism of Protein A. In particular, the peptide HWRGWV (SEQ ID NO: 1) was further characterized for its ability to isolate IgG from a variety of complex sources, including cell culture media, CHO cell culture supernatants, transgenic milk and whey, plant extract, and Cohn fraction II+III of human plasma. The product yields and purities that resulted from these experiments were always comparable to those obtained with Protein A media.

However, an issue that both protein ligands and synthetic peptide ligands face when used for the purification of polyclonal antibodies from human plasma is the action of proteolytic enzymes present therein, in particular trypsin and α-chymotrypsin. Trypsin is a serin protease that cleaves peptide chains at the carboxyl side of lysine and arginine residues. Chymotrypsin cleaves peptide chains at the carboxyl side of hydrophobic residues, such as tyrosine, tryptophan, and phenylalanine. Upon prolonged exposure and/or repeated to mammalian sera, either protein or peptide ligands are degraded by these endoproteases. To prevent degradation of Protein A by these endoproteases and hence the decrease of the lifetime of costly affinity resin, enzyme inhibitors are added to feed before injection. These inhibitors, however, represent a considerable additional cost themselves.

3. SUMMARY OF THE INVENTION

In particular non-limiting embodiments, the present invention provides a protease-resistant peptide with three to twenty amino acids capable of binding a biological and comprising one or more basic amino acid(s) and/or aromatic amino acids, wherein one or more of the amino acids is substituted with a non-naturally occurring amino acid analog. The non-natural amino acid analog may be one listed in Table 6.

The protease-resistant peptide may be a 4-mer, a 5-mer, a 6-mer, a 7-mer, an 8-mer, a 9-mer, a 10-mer, an 11-mer, a 12-mer, a 13-mer, a 14-mer, a 15-mer, a 16-mer, a 17-mer, an 18-mer, or a 19-mer. The protease-resistant peptide is a hexapeptide and have the sequence HWRGWV, HYFKFD and HFRRHL (SEQ ID NOS:1-3) prior to substitution with the non-naturally occurring amino acid(s).

The protease resistant peptide may have 1 non-naturally occurring amino acid. Alternatively, it may have 2, 3, 4, or 5 non-naturally occurring amino acids. The peptide may have 1 in 10 amino acids replaced by a non-naturally occurring amino acid (10%). Alternatively, it may have 1 in 19 amino acids replaced (~5%). It may have 2 in 10 amino acids replaced (20%) or 2 in 6 amino acids replaced (33%). It may be 50% non-naturally occurring amino acids, e.g., 3 in 6, or 4 in 8 etc.

If a naturally occurring peptide contains a glutamine, it may be replaced with N-γ-ethyl-glutamine to form the protease resistant peptide. If a natural counterpart contains glutamic acid, it may be replaced with carboxy-glutamic acid. If a naturally occurring peptide contains a proline, the protease resistant peptide may have a proline where a secondary hydrogen is replaced with a benzyl, an OH, or a phenyl. If a naturally occurring peptide contains a phenylalanine, the protease resistant peptide may have one or more aromatic hydrogens in the phenylalanine replaced with an amino group, an ethoxy group, an ethyl group, a methoxy group, a methyl group, an OH or a phenyl. If a naturally occurring peptide contains a tyrosine, the protease resistant peptide may have one or more aromatic hydrogens in the tyrosine replaced with an amino group, an ethoxy group, an ethyl group, a methoxy group, a methyl group, an OH or a phenyl. If the naturally occurring peptide contains an arginine, it may be replaced with citrulline or methylated to form the protease resistant peptide. Similarly, amino groups in the naturally occurring peptide may be replaced with methyl amino or dimethyl amino groups, e.g., the amino hydrogen(s) in lysine may be methylated to form the protease resistant peptide.

The protease-resistant peptide may be resistant to digestion by endopeptidases or exopeptidases. In one non-limiting embodiment, the endopeptidase may alpha-chymotrypsin or trypsin.

The invention also includes a solid support coupled to the protease-resistant peptide. The solid support may be a resin as a resin bead, e.g., Toyopearl.

In another embodiment, the invention provides a method of purification of a biological which comprises contacting the solid support with the protease resistant peptide with the biological under suitable conditions such that the biological binds to the solid support; washing the solid support and bound biological; and eluting the biological from the solid support so as to purify the biological. The biological may be an antibody.

The invention also provides a diagnostic kit comprising the solid support and the protease resistant peptide.

4. BRIEF DESCRIPTION OF THE FIGURES

FIG. 1. Cluster #1 of the sequences: a) HWRGWV, b) HFRRHL, (SEQ ID NOS: 1, 3) c) $HW_{Met}CitGW_{Met}V$, and d) $HF_{Met}CitCitHL$ (SEQ ID NOS: 4-5)

Figure 2:
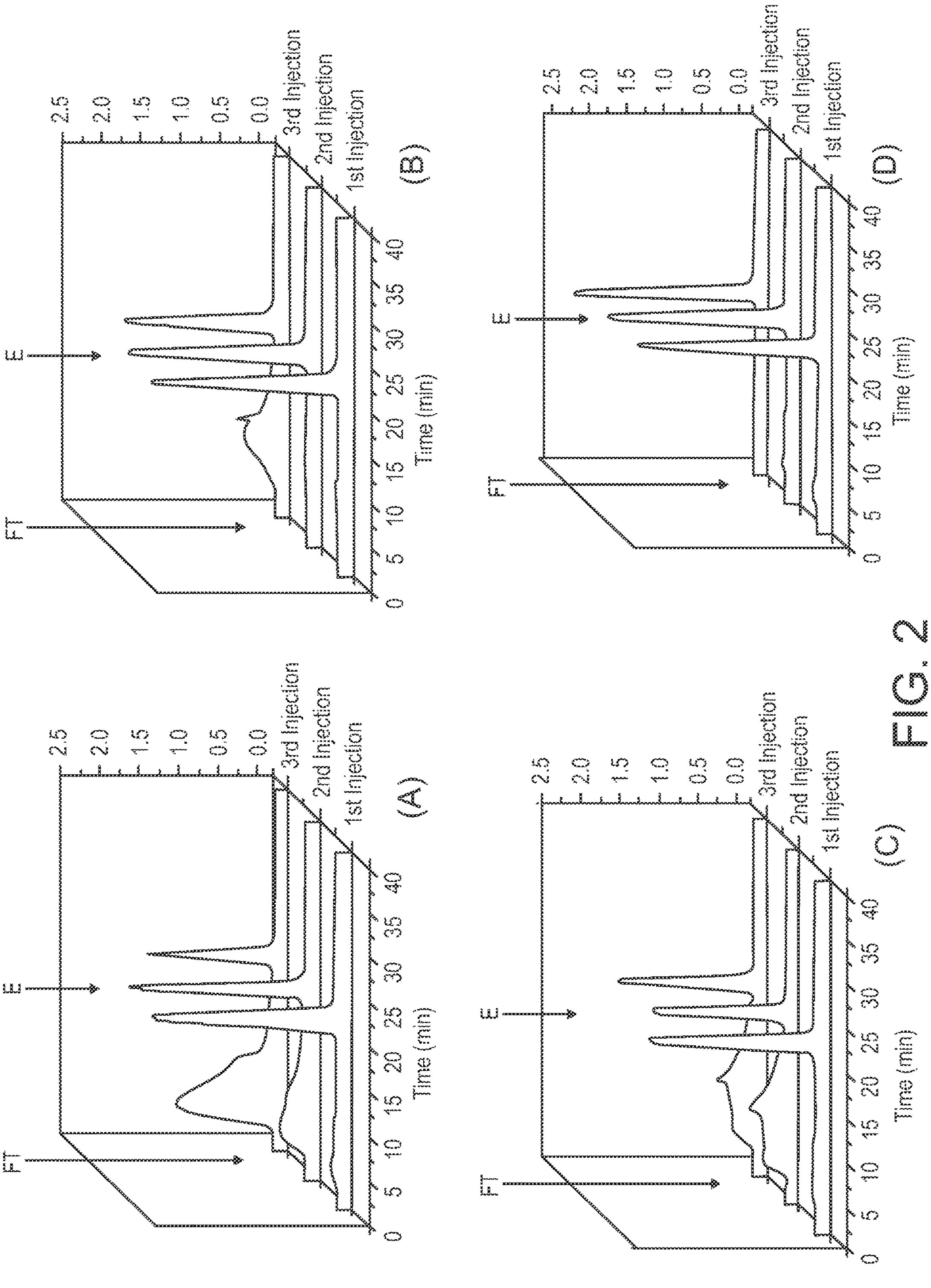

FIG. 2 panels (A)-(D) show proteolytic digests of natural peptide binders and modified peptide binders.

Figure 3:
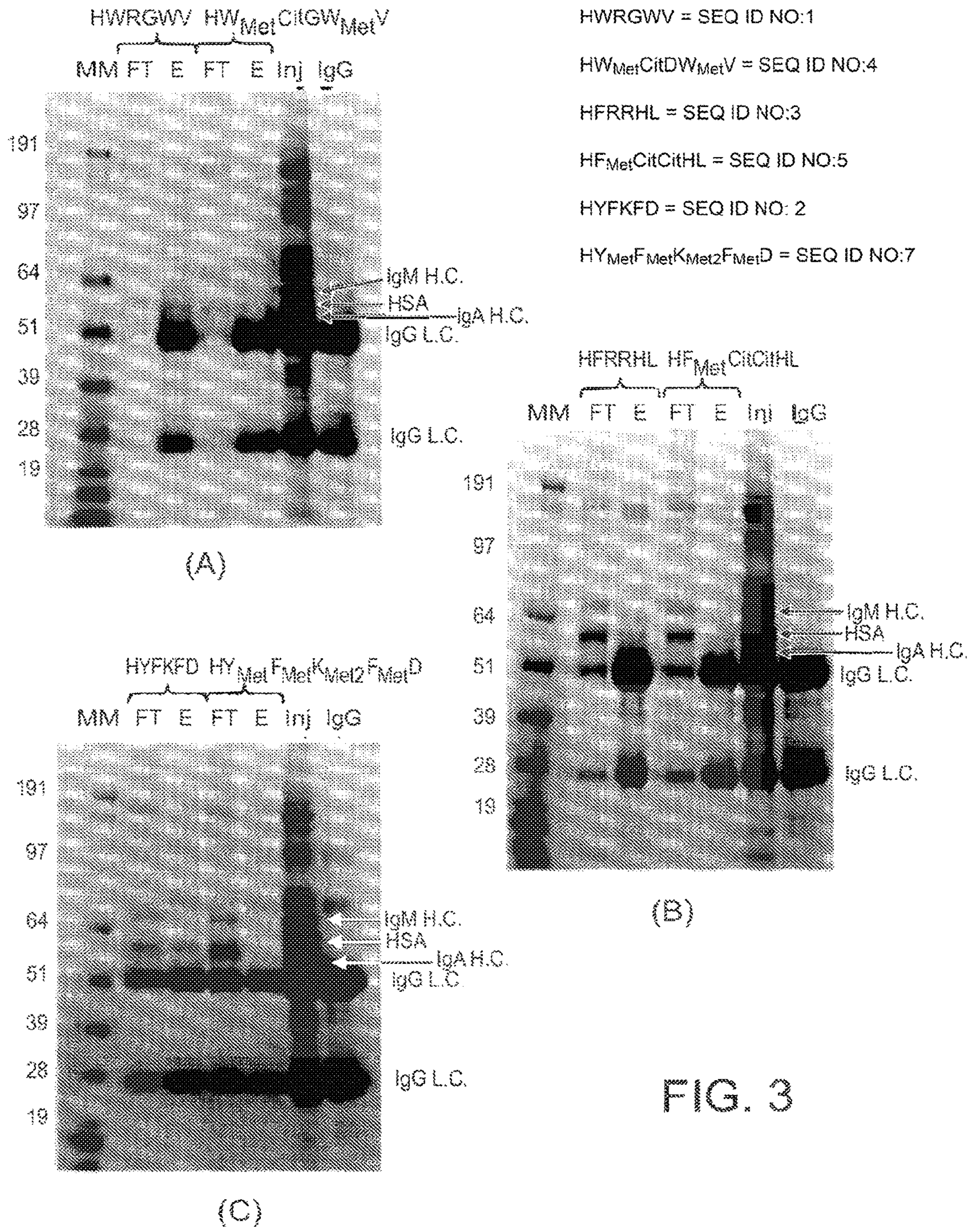

FIG. 3. SDS-PAGE (reducing conditions) of chromatographic purification of IgG from Cohn fraction II+III of human plasma using the adsorbents.

Figure 4:
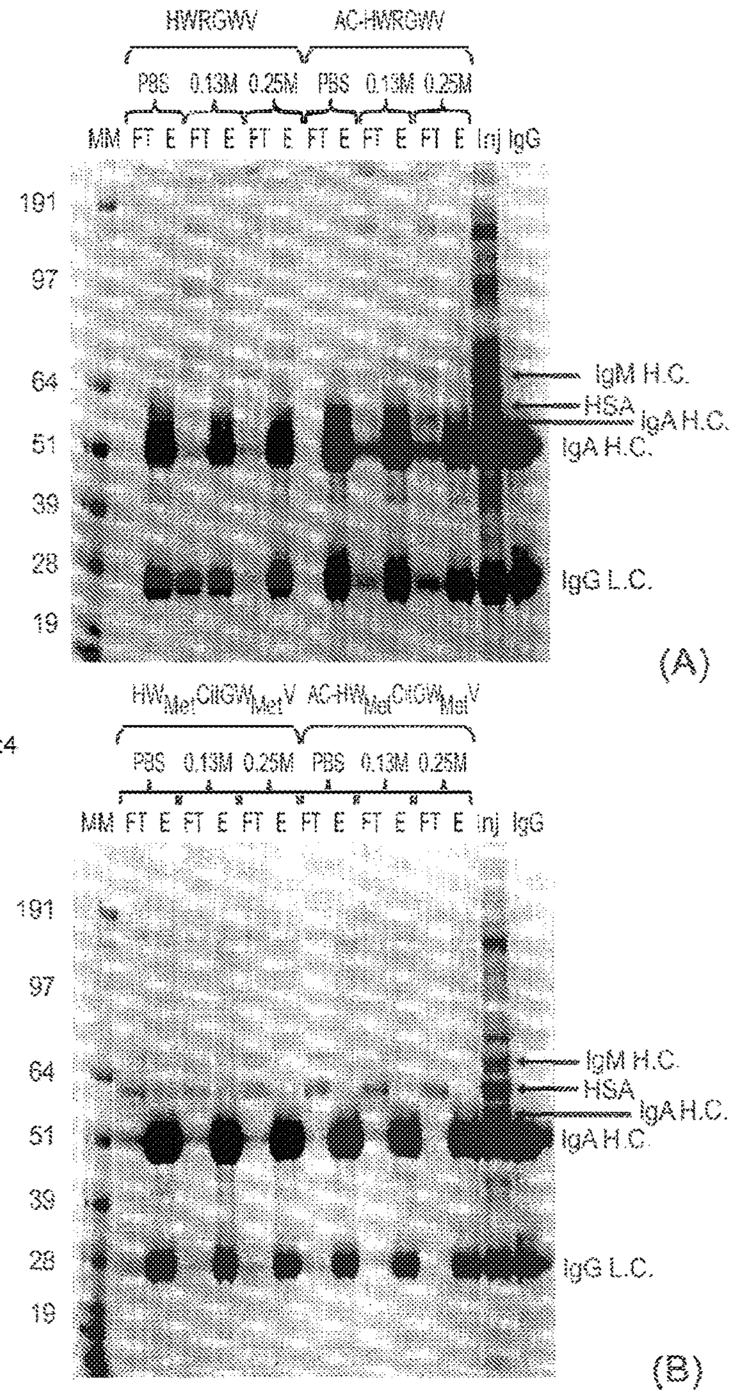

FIG. 4. SDS-PAGE (reducing conditions) of chromatographic purification of IgG from Cohn fraction II+III of human plasma performed at different salt concentration in the binding buffer.

5. DETAILED DESCRIPTION OF THE INVENTION

The purification of immunoglobulins from mammalian sera for therapeutic and research purposes is an issue of considerable relevance in biotechnology and biomanufacturing [1, 2].

Plasma-derived polyclonal intravenous immunoglobulin (IVIG) preparations have been successfully applied to the prophylactic prevention of infectious diseases in immunodeficient patients and find increasing use against autoimmune and inflammatory disorders [3,4]. To date, IVIG is the major plasma product on the global blood product market, with a steadily increasing annual consumption [5]. Further, polyclonal antibodies derived from the serum of immunized animals are also currently employed in medical research for developing immunoassays, therapeutic treatments and new strategies of drug delivery [6-9]. Serum can also be a source of monoclonal antibodies, as is the case in hybridoma technology, which, although quite dated, is still a powerful research tool for the development of monoclonal antibodies [10]. As hybridoma colonies are grown in culture media mainly with high concentrations of bovine serum, the purification of monoclonal antibodies from these fluids resembles in fact the recovery of polyclonal antibodies from animal sources [11]. Protein A and Protein G, the most commonly used affinity ligands for antibody purification, are not well suited for this type of antibody purification [12, 13]. Besides the known issues of high cost, low chemical stability, immunogenicity, and harsh elution conditions caused by the low dissociation constant (~$10^{-8}$ M), there are some additional concerns [14, 15]. Protein A does not bind human $IgG_3$ subclass, shows weak binding of mouse $IgG_1$ and bovine $IgG_1$, and does not bind goat and mouse IgG or subclasses of chicken IgY [16]. Protein GS while binding all human IgG subclasses and the majority of animal antibodies, also captures albumin, by far the major protein constituent in plasma and serum, and hence it is not normally used for antibody purification from plasma [17]. Engineered forms of Protein G without the albumin binding site have been developed [18], but they are very costly and the issues of stability and immunogenicity remain a concern. To overcome these issues, synthetic ligands have been developed for antibody purification, which are more affordable and chemically robust, less toxic and less immunogenic when compared to protein ligands [19, 20].

Our research group has identified three peptide ligands, HWRGWV, HYFKFD and HFRRHL (SEQ ID NOS: 1-3), which bind IgG through the Fc portion, thus mimicking the binding mechanism of Protein A [21-23]. These sequences bind all human antibody subclasses as well as many animal (bovine, mouse, rabbit goat, llama, and avian) antibodies, and have been used for the purification of monoclonal and polyclonal antibodies from a variety of sources, including Cohn fraction II+III of human plasma [24-26]. In all these studies, product yield and purity were always found to be comparable to those given by Protein A. Yet, owing to their milder binding strength ($K_D$~$10^{-5}$-$10^{-6}$ M), they allow antibody elution from affinity columns under gentler conditions (pH 4.0-5.0), thus preventing aggregation and maintaining activity. Much work has also been carried out to increase the chemical stability and dynamic binding capacity (DBC) of these peptide ligand adsorbents. As a result of these optimization studies, the HWRGWV-Toyopearl (SEQ ID NOS: 6) (adsorbent showed high resistance to 0.5M NaOH over continuous cycles of use and DBC values in the range of 50 g/L [27, 28]. These ligands could hence enable the development of industrial scale affinity purification of monoclonal and polyclonal antibodies from serum and plasma.

A problem that both protein and synthetic peptide ligands face when used for the purification of polyclonal antibodies from animal plasma is the presence of proteolytic enzymes, such as trypsin and α-chymotrypsin [29, 30]. These proteases cleave peptide chains at the carboxyl end of basic (arginine and lysine) and aromatic (tryptophan, phenylalanine, and tyrosine) amino acids respectively [31, 32]. Upon prolonged exposure of the affinity adsorbent to serum, trypsin and α-chymotrypsin cause substantial degradation of protein or peptide ligands with consequent loss of binding capacity. For protein ligands, like Protein A/G, this problem is aggravated by the release of immunogenic fragments in the product mainstream. As a preventive measure, protease enzyme inhibitors are often added to the feed mixture before injection [33]. These inhibitors, however, are costly and need to be removed from the final product.

A radical solution to these issues is to produce variants of peptide ligands comprising non-natural amino acids. These variants are expected to combine good target affinity and selectivity with high resistance against proteases. Verdoliva et al. have proposed the synthesis of a peptide ligand using D-stereoisomers of amino acids, which, unlike the naturally occurring L-forms, are not recognized and attacked by proteases [34, 35]. D-amino acids, however, are very costly and are prone to other kinds of chemical degradation, such as those caused on the amino acid functional groups by acid and alkaline solutions used for protein elution and resin sanitization respectively [36-39]. To overcome these obstacles, chemically modified forms of L-amino acids can be employed instead of D-amino acids to produce peptide variants that, while retaining the target affinity and selectivity of the original sequences, exhibit high enzymatic resistance and chemical stability. To this end, a method is herein presented for the design and identification of these ligands which comprises three steps: 1) design of a virtual library of variants of known peptide ligands using non-natural amino acids, 2) library screening in-silico against the target biomolecule by molecular docking simulations, 3) synthesis of the selected variants on chromatographic resins and testing of the resulting adsorbents for target binding and resistance to proteases. Tryptophan, phenylalanine, tyrosine, and lysine in the antibody binding peptides HWRGWV, HYFKFD, and HFRRHL (SEQ ID NOS: 1-3) were replaced with alkylated analogs, while citrulline was used in place of arginine.

Other variants were created using $N_{in}$-formyl-tryptophan and 4-carbamoyl-phenylalanine, as well as by replacing glycine with aspartic acid in HWRGWV (SEQ ID NO: 1). The library was then screened against the known HWRGWV (SEQ ID NO: 1) binding site in the pFc region of IgG (Ser383-Asn389) using the docking software HADDOCK (version 2.1) [40, 41]. This program simulates protein-peptide interaction and through external software estimates the free energy of binding based on the evaluation of van der Waals interactions, hydrogen bonding, deformation penalty, hydrophobic effects, atomic contact energy, softened van der Waals interactions, partial electrostatic, additional estimation of the binding free energy, dipole-dipole interactions, and the presence of water [40-45]. The selected sequences were synthesized directly on the polymethacrylate-based chromatographic resin Toyopearl AF-Amino-650M and tested for IgG binding and resistance against trypsin and α-chymotrypsin. The sequences $HW_{Met}CitGW_{Met}V$, $HF_{Met}CitCitHL$, and $HY_{Met}F_{Met}K_{(Met)2}F_{Met}D$ (SEQ ID NOS: 4, 5, 7) were chosen for purifying polyclonal antibodies (IVIG) from Cohn fraction II+III of human plasma.

Finally, a study on the effect of conductivity of the binding buffer on IgG yield and purity was performed to compare the binding mechanism of the parental peptide HWRGWV (SEQ ID NO: 1) and its variants $HW_{Met}CitGW_{Met}V$ and Ac-$HW_{Met}CitGW_{Met}V$ (SEQ ID NO: 8-9). The latter was shown to attain higher IVIG yield and purity than HWRGWV (SEQ ID NO: 1) at lower conductivity of the binding buffer, thereby offering significant cost reduction for large scale downstream process.

In one, non-limiting embodiment, the method may comprise four steps:

1—Design of a library of variants of a known peptide ligand using non-natural modified amino acids;

2—Selection of a subset of ligands by screening the library of peptide variants against the target biomolecule via molecular docking simulations;

3—Synthesis of the selected ligands by conventional Fmoc/tBu coupling chemistry on chromatographic resins;

4—Chromatographic testing of the affinity adsorbents for: a) binding of the target biomolecule and b) resistance to proteolytic enzymes and chemical agents employed in the chromatographic procedure.

1 Design of Variants of the Peptide Ligand HWRGWV (SEQ ID NO: 1)

A virtual library of peptide variants (Table 1) was designed.

TABLE 1

Peptides used in Molecular Modeling Study

| Peptide | SEQ ID NO: |
|---|---|
| HFRRHL | 3 |
| $HF_{Met}CitCitHL$ | 5 |
| HWCitGWV | 10 |
| HWRGWV | 1 |
| $HW_{Met}CitGW_{Met}V$ | 8 |
| $HW_{Met}RGW_{Met}V$ | 11 |
| HYFKFD | 2 |
| $HW_{For}CitGW_{For}V$ | 12 |
| $HY_{Met}F_{Met}K_{Met}F_{Met}D$ | 13 |
| $HF_{Carb}CitCitHL$ | 14 |
| $HW_{Met}CitDW_{Met}V$ | 4 |
| $HY_{Met}F_{Met}K_{Met2}F_{Met}D$ | 7 |

2—Molecular Modeling

The coordinate files for the peptide variants were generated using PYMOL [The PyMOL Molecular Graphics System, Version 1.2r3pre, Schrödinger, LLC]. Parameter and topology files for the modifications were determined by observing the closest matching natural residues and copying those qualities to design the non-natural amino acid entry. $N_{in}$-methylated and formylated tryptophan were designed based on the parameter and topology files for standard tryptophan residue. 4-Methyl-, 4-methoxy-, and carbamoyl-phenylalanine were designed based on the parameter and topology files for standard phenylalanine residue, in particular the carbamoyl functionality was obtained from asparagine. Citrulline was modeled based upon arginine's carbon delta and asparagine. Files for methylated and dimethylated lysine, Lys(Me) and $Lys(Me)_2$, were already coded in HADDOCK. The partial charge on a single atom was assigned so as to maintain electrical neutrality on the functional groups, identically to all other parameter and topology files for natural amino acids in HADDOCK. Parameter and topology file modifications were checked against submission to the PRODRG server for verification of the topology and parameter files for the amino acid modifications. The coordinate file for hIgG was obtained from the RCSB Protein Data Bank (PDB, 1FCC) [Structure. 1995 Mar. 15; 3(3):265-78. Crystal structure of the C2 fragment of streptococcal protein G in complex with the Fc domain of human IgG. Sauer-Eriksson A E, Kleywegt G J, Uhlén M, Jones T A.]. The residues Ser383-Asn389 (SNGQPEN) (SEQ ID NO: 15) on hIgG were defined as "active" and used as a target region for ligand docking. Protein A was included in the target PDB file as a global restraint to prevent interaction between the peptide ligands and the Protein A binding site (residues 341-443) on hIgG. Molecular modeling was performed using the program HADDOCK (version 2.1) [S. J. de Vries, A. D. J. van Djik, M. Krzeminski, M. van Dijk, A. Thureau, V. Hsu, T. Wassenaar, A. M. Bonvin, Proteins: Struc. Funct. & Bioinformatic 69 (2007) 726. and C. Dominguez, R. Boelens, A. M. Bonvin, J. Am. Chem. Soc. 125 (2003) 1731.]. For each peptide variant, residues 1-2 were targeted to residues 389-387 of hIgG, residues 3-4 were targeted to residue of hIgG 386-383, while residues 5-6 were not targeted. Default HADDOCK parameters were used in the docking procedure. The resulting docked structures were grouped in clusters, by assigning a minimum cluster size of 4 and an RMSD (root-mean-square-distance) of no greater than 2.5 Å using the program ProFit (www.bioinf.org.uk/software/profit/). All the clusters selected for each sequence based on visual inspection of the lowest energy docked solution were analyzed according to twelve scoring functions grouped in three families, dComplex, XScore (HP- Score, HMScore, HSScore, −log(Kd), and $\Delta_r G$), and FireDock (global, attractive VdW, repulsive VdW, ACE, and hydrogen bond) [Wang, R., Y Lu, and S. Wang, Comparative evaluation of 11 scoring functions for molecular docking. J Med Chem, 2003. 46(12): p. 2287-303 and Andrusier, N., et al., Principles of flexible protein-protein docking. Proteins, 2008. 73(2): p. 271-89 AND Mashiach, E., et al., FireDock: a web server for fast interaction refinement in molecular docking. Nucleic Acids Res, 2008. 36(Web Server issue): p. W229-32. and Liu, S., et al., A physical reference state unifies the structure-derived potential of mean force for protein folding and binding. Proteins, 2004. 56(1): p. 93-101]. A ranking of the sequences was thus compiled, listing the sequences ordered upon the scoring value obtained according to the respective function. This ranking wa finally totaled and averaged to obtain a final list of sequences, where lower score indicates higher affinity.

DEFINITIONS

The term "biological" includes biopharmaceuticals or biotherapeutics, such as therapeutic proteins. These may be protein therapeutics with enzymatic and/or regulatory activity; or proteins with special binding activity, such as monoclonal antibodies or Fc-fusion proteins; or protein vaccines; or diagnostic proteins. Biologicals may be isolated from living organisms, such as blood factors, or produced by recombinant technology. See Strohl and Knight, *Curr Opin Biotech*, (2009) 20:668-672, the contents of which are hereby incorporated by reference in its entirety. As used herein, biological also includes viruses and microorganisms such as bacteria, fungi, unicellular or multicellular organisms. In some non-limiting embodiments, a biological may be a pathogenic protein such as a prion, or a pathogenic microorganism such as bacteria, and the like.

Nelson et al. and Nieri et al. recently reviewed therapeutic antibodies either the market or in clinical development and current techniques for their production. Nelson et al. 2010 *Nat Rev Drug Disc* 9 767-774; Nieri et al. 2009 *Curr Top Med Chem* 16 753-779.

Fully human antibodies also may be produced via CHO cell culture and by transgenic animals and plants. Full-size human monoclonal antibodies are now extracted by milk of transgenic animals (e.g., cows, goats). Redwan 2009 *J Immunoass Immunochem* 30 262-290. Also plants, like tobacco, are used for making antibodies. Tobacco is relatively easy to transfect using the tobacco virus. Yusibov et al. 2011 *Hum Vacc* 7(3) 313-321.

A "biopolymer" is a polymer of one or more types of repeating units. Biopolymers can be found in natural biological systems and particularly include oligosaccharides and polysaccharides, peptides (which term is used to include polypeptides and proteins), and polynucleotides (which term is used to include DNA and RNA), or can be produced by artificial biosynthesis, such as peptoids and peptide nucleic acids (PNA). As used herein, the term "biopolymer" includes synthetic compounds having biological activity, such as analogs of naturally occurring compounds composed of or containing amino acids or amino acid analogs, sugars or sugar analogs, or nucleotides or non-nucleotide groups.

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., The Proteins, Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine: (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine.

The term "solid support" means materials with a hydrophilic macroporous material, of either polymer or inorganic nature, may be used in the present invention. Solid supports include inorganic materials, organic materials, and combinations thereof. It may be a hydroxylated solid support or a hydroxylated composite solid support. The solid support may be an acrylamide derivative, agarose, cellulose, chitin, chitosan, dextran, glass, magnetite, polyacrylate, polyacrylamide, polystyrene, polyvinyl alcohol, silica, silicon, zirconia, and combinations thereof. The solid support material may be in the form of porous beads, which may be spherical. Alternatively, the support may be particulate or divided form having other regular or irregular shapes. Other examples of suitable solid support materials include membranes, semipermeable membranes, capillaries, microarrays, monolites, multiple-well plates comprised of alumina, alumina supported polymers, or polysaccharides. Solid supports of the present invention may be rigid or non-rigid flexible materials, such as a fabric which may be woven or non-woven. Suitable non-rigid flexible materials might be membranes (cast, non-woven, or micro- or nano-fibers produced with different techniques known in the art).

Preferred solid support materials are those having minimal non-specific binding of proteins and that are physically and chemically resistant to the conditions used for organic synthesis as well as for the purification process employed in this invention such as changes in pH and ionic strength. The solid support used in the present invention may be a polymer of acrylate. Examples of acrylate polymers include, but are not limited to, polymethacrylate, polyhydroxy methacrylate, polymethyl methacrylate, polyacrylamide, polyacrylonitrile and other acrylate derivatives. In a preferred non-limiting embodiment, the solid support is a methacrylate polymer.

Compositions and Kits

The invention provides compositions and kits for detecting and/or measuring types and levels of a particular target of interest using the protease-resistant binder peptide described herein in an assay which may be a diagnostic assay. Kits for carrying out the assays of the invention typically include, a suitable container means, (i) a probe that comprises a protease-resistant binder peptide of the invention; (ii) a label for detecting the presence of the probe; and (iii) instructions for how to measure the target of interest. The kits may include one or more protease-resistant binder peptides, e.g., a first protease-resistant peptide and/or second and/or third and/or additional protease-resistant peptide specifically binds to and recognizes a target of interest. The container means of the kits will generally include at least one vial, test tube, flask, bottle, syringe and/or other container into which a first protease-resistant peptide of the present invention may be placed and/or suitably aliquoted. Where a second and/or third and/or additional component is provided, the kit will also generally contain a second, third and/or other additional container into which this component may be placed. Alternatively, a container may contain a mixture of more than one protease-resistant peptide, each reagent specifically binding a different marker in accordance with the present invention. The kits of the present invention will also typically include means for containing the protease-resistant peptide probes in close confinement for commercial sale. Such containers may include injection and/or blow-molded plastic containers into which the desired vials are retained.

The kits may further comprise positive and negative controls, as well as instructions for the use of kit components contained therein, in accordance with the methods of the present invention.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

Synthesis of Selected Peptide Variants

Materials

Protected amino acids and coupling agents for peptide synthesis were purchased from ChemImpex Inc. (Wood Dale, Ill., USA). Trypsin, α-chymotripsin, diisopropylethylamine (DIPEA), piperidine, trifluoroacetic acid (TFA), triisopropylsylane (TIPS), ethanedithiol (EDT), phenylsilane, thioanisole, sodium diethyldithiocarbamate, indole, phosphate buffer saline (PBS) pH 7.4, and Kaiser test kit were from Sigma Aldrich (Saint Louis, Mo., USA). N,N'-dimethylformamide (DMF), dichloromethane (DCM), HPLC grade acetonitrile and water, sodium acetate, sodium chloride, acetic acid glacial were purchased from Fisher Scientific (Pittsburgh, Pa., USA). Toyopearl AF-Amino-650M resin was purchased from Tosoh Bioscience (King of Prussia, Pa., USA).

Methods

Each of the selected sequences were synthesized on 200 mg of Toyopearl AF-Amino-650M resins (d=75-150 micron, amino group density=0.4 mmol/g). Each amino acid coupling step was conducted for 25 min in a polypropylene tube fitted with a Teflon frit under continuous nitrogen flow and at a temperature of 35 C. After rinsing the resin in DMF for 10 min, one coupling was performed with Fmoc-Ala-OH (3 eq. molar excess as compared to the base resin functional density), HCTU (3 eq.) and DIPEA (6 eq.) in 3 mL of dry DMF. An acetylation step with acetic anhydride and DIPEA (50 eq.) in 4 mL of DMF was carried out for 30 min at room temperature. The Fmoc protection was then removed by incubating with 5 mL of 20% piperidine in DMF for 20 min.

The peptide sequences were synthesized via conventional Fmoc/tBu strategy. For each amino acid, an anhydrous DMF solution (2.5 mL) of Fmoc-amino acid (2 eq.), HCTU (2 eq.) and DIPEA (4 eq.) was added to the resin. Two couplings were performed for each amino acid to saturate all the available amino groups, as monitored by Kaiser test. The Fmoc protection on the last amino acid was removed with 5 mL of 20% piperidine in DMF for 20 min and each batch of resin was split in two aliquots, of which one was acetylated as indicated above. After rinsing the resins with DMF and DCM, peptide deprotection was performed using a cleavage cocktail containing TFA/DCM/indole (70/28/2) for 1.5 hours. Resins were then copiously rinsed with DCM and DMF and finally dried under vacuum.

Chromatographic Testing of the Affinity Adsorbents

Materials

Human polyclonal immunoglobulin G (IgG) in lyophilized form was purchased from Equitech-Bio, Inc. (Kernville, Tex., USA). All studies were carried out at room temperature. A Waters 626 LC system integrated with 2487 UV detectors (Waters, MA, USA) was used for all chromatography runs. Microbore stainless steel columns 30 mm long×2.1 mm I.D. were from Altech-Applied Science (Somerset, Pa., USA). All experiments were carried out at room temperature.

Chromatographic Evaluation of IgG Binding and Resistance to Proteolytic Enzymes of the Peptide Ligands All resins (35 mg each) were packed in a 30 mm×2.1 mm I.D. Microbore column (0.1 mL) (Alltech-Applied Science, Somerset, Pa., USA) and swollen with 20% v/v methanol. After equilibration with PBS, pH 7.4, three IgG binding tests were performed using a 10 mg/mL solution of hIgG in PBS. Between each binding test, the resin was contacted with a 0.15 mg/mL solution of either trypsin or α-chymotrypsin in Tris HCl buffer, pH 8.5. The chromatographic protocol employed for all five injections was as follows. One hundred microliters of feed sample was loaded onto the column at a flow rate of 0.05 mL/min (87 cm/h). After a washing step with 2 mL of equilibration buffer at a flow rate of 0.2 mL/min (348 cm/h), elution was performed with 4 mL of 0.2M acetate buffer pH 4.0 at a flow rate of 0.4 mL/min (696 cm/h). Finally, the adsorbent was regenerated with 4 mL of 0.85% phosphoric acid. The adsorbents HWRGWV-, HYFKFD-, and HFRRHL-Toyopearl (SEQ ID NOS: 6, 16, 17) resins were used as controls. The effluent was monitored by absorbance at 280 nm.

Purification of IVIG from Cohn Fraction II+III of Human Plasma Using the Adsorbents $HW_{Met}CitGW_{Met}V$-, $HY_{Met}F_{Met}K_{(Met)2}F_{Met}D$- and $HF_{Met}CitCitHL$-Toyopearl (SEQ ID NOS: 18-20) Resins Cohn fraction II+III was dissolved in PBS, pH 7.4 to obtain an approximate IgG concentration of 5 mg/mL and filtered sequentially using a 0.44 μm and a 0.22 μm filter from Pall Corporation (Port Washington, N.Y., USA). Each peptide resin was packed and swollen as described before. After equilibration with PBS buffer containing 0.25M NaCl, 100 μL of feed sample was loaded onto the column at a flow rate of 0.05 mL/min (87 cm/h). After washing the column with 2 mL of equilibration buffer at a flow rate of 0.2 mL/min (348 cm/h), elution was performed with 4 mL of 0.2M acetate buffer pH 5.0 at a flow rate of 0.4 mL/min (696 cm/h). Cleaning and regeneration were performed using 4 mL of 0.85% phosphoric acid followed by a wash with 4 mL of 2M urea in acetate buffer (pH 4.0). Toyopearl AF-rProtein A-650F resin was used as a positive control. As per manufacturer's instructions, the chromatographic protocol comprised binding with PBS, pH 7.4 (at a flow rate of 0.05 mL/min) and elution with 0.1M Glycine buffer pH 2.5 (at a flow rate of 0.4 mL/min). The effluent was monitored by absorbance at 280 nm. Fractions were collected and used for analysis of IgG purity and yield as described below.

Effect of Conductivity on the IgG Purification from Cohn Fraction II+III of Human Plasma Using the Adsorbents Ac-HWRGWV- and Ac-$HW_{Met}CitGW_{Met}V$-Toyopearl (SEQ ID NOS: 21-22) Resins The resins were packed and swollen as described before, while the Cohn fraction II+III for the injection was prepared as described before. The effect of conductivity of the binding buffer was studied at 0, 0.135 and 0.25 M NaCl added to PBS. After equilibration with binding buffer, 100 μL of feed was loaded onto the column at a flow rate of 0.05 mL/min (87 cm/h). Chromatographic protocol and fraction collection were done as above described.

Sample Analysis for Yields and Purities

The amount of IgG in the collected fractions was quantified by HPLC using 1 mL HiTrap Protein G column. The yield of IgG was calculated as the ratio of IgG eluted to total IgG loaded. The purity of IgG in the eluted fractions was determined by sodium dodecyl sulfate polyacrylamide gel electrophoresis (SDS-PAGE) under reducing conditions using NuPAGE® Novex 4-12% Bis-Tris gels in a Xcell SuperLock™ Mini-Cell system (LifeSciences, Carlsbad, Calif., USA). Sample preparation was done by adding 5 μL of NuPAGE® LDS buffer and 2 μL of NuPAGE® reducing agent to 13 μL of sample and boiling the resulting mixture for 10 min. Gels were Coomassie-stained by using SimpleBlue™ SafeStain. The IgG purity was determined by densitometric analysis of Coomassie-stained gels by means of ImageJ 1.32j software (National Institutes of Health, Bethesda, Md., USA).

The purity of the product was calculated as the fraction of the total area equivalent to the IgG bands at 25 and 50 KDa.

Results and Discussion

Seven non-natural amino acids were chosen for this study, namely $N_{in}$-methyl-tryptophan, $N_{in}$-formyl-tryptophan, 4-methyl-phenylalanine, 4-carbamoyl-phenylalanine, O-methyl-tyrosine, e, e-dimethyl-lysine, and citrulline. The parameter and topology files of these residues were created using the files available for each corresponding standard amino acid as base structures. The modifications on the side chain functional groups were introduced by copying the closest matching moiety on a standard residue and adjusting the charge distribution to ensure electrical neutrality. The resulting parameter and topology file modifications were checked against submission to the PRODRG server, a standard verification process for parameterization of amino acid modifications. Hence, a virtual library of peptide sequences was created and screened against hIgG using HADDOCK 2.1 [S. J. de Vries, A. D. J. van Djik, M. Krzeminski, M. van Dijk, A. Thureau, V. Hsu, T. Wassenaar, A. M. Bonvin, Proteins: Struc. Funct. & Bioinformatic 69 (2007) 726. and C. Dominguez, R. Boelens, A. M. Bonvin, J. Am. Chem. Soc. 125 (2003) 1731.].

In order to perform a physically meaningful docking, a few constraints based on previous findings by Yang et al. were introduced in the simulations. First, MS analysis of protease digests of the Fc fragment of hIgG revealed a putative binding sequence for HWRGWV (SEQ ID NO: 1) on the pFc segment, comprising the loop Ser383-Asn 389 (SNGQPEN), which was found to be distinct from the Protein A binding site (residues 341-443 on hIgG) [23]. This result was consistent with the observation that the peptide HWRGWV (SEQ ID NO: 1) does not compete with Protein A for hIgG binding. Second, the basic motif comprising the first three amino acids of the peptide sequence, that is, histidine followed by an aromatic and a basic residue, is crucial in IgG binding. This has been evidenced by the consensus found in the sequences HWRGWV, HYFKFD, and HFRRHL (SEQ ID NOS: 1-3) identified by screening a solid phase library of hexapeptides [21]. Based on this homology, it is reasonable to assume that the two sequences HYFKFD (SEQ ID NO: 2) and HFRRHL (SEQ ID NO: 3) interact with the same binding site of hIgG as HWRGWV (SEQ ID NO: 1).

Finally, since the C-terminus of the peptide is tethered with the surface of the chromatographic resin, it is rather likely that residues 5 and 6 of the hexapeptide ligands play only a modest role in targeting IgG. Based on this information, the residues Ser383-Asn389 on hIgG were defined as "active" and used as target for ligand docking. All active residues exhibit a relative solvent accessibility higher than 40%, as defined by the program NACCESS [Campbell & Thornton (1991) J. Mol. Biol. 220, 507-530].

Further, on each peptide variant, residues 1-2 were targeted to residues 389-387 of hIgG, residues 3-4 were targeted to residues 386-383, while residues 5 and 6 were left unassigned and allowed to interact with any residues on IgG it wishes to do so. To minimize bias in the validation, the following set of general criteria was devised for selecting the complexes resulting from docking simulations: 1) All the structures determined for each sequence in the final stage of molecular docking were clustered based on a stringent RMSD (root-mean-square-distance) cutoff of 2.5 Å, whereas default clustering RMSD cutoff is usually set at 7.5 Å, and a minimal cluster size of 4 structures. 2.) The structures used for the analysis were the most energetically favored docked structure from each cluster. 3) Each cluster was analyzed using the scoring methods dComplex, XScore, and FireDock, empirical scoring function that estimate the binding affinity of a given protein-ligand complex of known three-dimensional structure.

These functions account for van der Waals interactions, hydrogen bonding, deformation penalty, hydrophobic effects, atomic contact energy, softened van der Waals interactions, partial electrostatics, additional estimations of the binding free energy and dipole-dipole interactions

[Wang, R., Y Lu, and S. Wang, *Comparative evaluation of 11 scoring functions for molecular docking*. J Med Chem, 2003. 46(12): p. 2287-303 and Andrusier, N., et al., *Principles of flexible protein-protein docking*. Proteins, 2008. 73(2): p. 271-89 and Mashiach, E., et al., *FireDock: a web server for fast interaction refinement in molecular docking*. Nucleic Acids Res, 2008. 36(Web Server issue): p. W229-32. and Liu, S., et al., *A physical reference state unifies the structure-derived potential of mean force for protein folding and binding*. Proteins, 2004. 56(1): p. 93-101]. The hybrid approach of using multiple scoring methods was adopted as not to bias the results to one particular method. Each cluster was ranked according to its individual score in the respective scoring method and the individual rankings thus produced were totaled and averaged. The final rank for the original sequences and several selected variants is reported in Table 2. FIG. 1 shows a cluster #1 of the sequences: a) HWRGW, b) HFRRHL, c) HW$_{Met}$CitGW$_{Met}$V, and d) HF$_{Met}$CitCitHL (SEQ ID NOS: 1, 3, 4, 5)

Although docking simulations generated multiple clusters per sequence, in many cases cluster #1 showed the highest number of structures, as well as lowest average value from the hybrid scoring method described above. Such reproducibility is indicative of well-performed docking simulations and allows excluding outliers that appear at significantly lower energies than the main cluster. By comparing HWRGWV and HFRRHL with their variants HWCitGWV and HFCitCitHL (SEQ ID NOS: 1, 3, 10, 23), it was noted that the former have the most contacts with the target antibody, while the latter have the most hydrogen bonds. This indicates a slight different binding mechanism of the variants as compared to the original sequences that contain arginine, particularly with respect to the electrostatic component. In fact, by replacing positively charged (at pH 7.4) arginine with electrically neutral citrulline, the electrostatic component of binding is considerably reduced. On one hand, this causes the predicted free energy of binding of the peptide variants to the target antibody to be lower as compared to the original sequences, which in turn suggests that the former might have a lower binding capacity than the latter. On the other hand, it makes the variant potentially less prone to nonspecific electrostatic binding of negatively charged proteins, albumin in particular, which lowers the product purity. These differences have direct implications on the chromatographic protocol, especially on the effect of conductivity of the binding buffer on the IgG yield and purity, and are discussed herein.

Other variants of HWRGWV (SEQ ID NO: 1) and HFRRHL (SEQ ID NO: 3) were designed using formyl-tryptophan and carbamoyl-phenylalanine, neither of which, however, obtained a good score. One more variant HW$_{Met}$CitGW$_{Met}$V (SEQ ID NO: 4), was created by replacing glycine with aspartic acid for the purpose of increasing affinity by potentially forming hydrogen bonds between the aspartic acid and the residues 383-386 (SNGQ) (SEQ ID NO: 24) on IgG. Against expectations, however, this sequence obtained a lower score. HYFKFD and its two variants HY$_{Met}$F$_{Met}$K$_{Met}$F$_{Met}$D and HY$_{Met}$F$_{Met}$K$_{(Met)2}$F$_{Met}$D (SEQ ID NOS: 2, 13, 7) were also run, but obtained, on average, worse scores, indicative of lower affinity as compared to HWRGWV (SEQ ID NO: 1), HFRRHL (SEQ ID NO: 3), and their variants.

The sequences listed in Table 2 were synthesized on Toyopearl resin, all at the approximate density of 0.12 meq/g. Each adsorbent thus obtained was packed into a chromatographic column (0.1 mL) and tested for IgG binding. Flowthrough and elution fractions were collected and analyzed by Protein G chromatography to determine IgG yield (Table 2). The comparison between the average rank and the yield for each sequence indicates good agreement between the docking simulations and the experimental results of antibody binding. This confirms that the design of the virtual library, the assignment of docking constraints, and the analysis of the simulation results were well performed and form an effective strategy for the selection of peptide variants.

TABLE 2

Predicted free energy of binding, docking rank, and IgG yield obtained for the original peptide sequences and their variants. (SEQ ID NOS: ***)

| SEQ ID NO: | Sequence | DiG (kcal/mol) | Average rank | IgG yield |
|---|---|---|---|---|
| 3 | HFRRHL | −6.96 | 2.00 | 93% |
| 5 | HFMetCitCitHL | −6.57 | 2.00 | 90% |
| 10 | HWCitGWV | −6.64 | 4.00 | 91% |
| 1 | HWRGWV | −6.37 | 5.00 | 95% |
| 8 | HWMetCitGWMetV | −6.71 | 9.00 | 90% |
| 11 | HWMetRGWMetV | −6.38 | 10.00 | 91% |
| 2 | HYFKFD | −5.66 | 14.00 | 78% |
| 12 | HWForCitGWForV | −5.41 | 16.17 | 75% |
| 13 | HYMetFMetKMetFMetD | −5.17 | 18.67 | 49% |
| 14 | HFcarbCitCitHL | −5.03 | 21.50 | 53% |
| 4 | HWMetCitDWMetV | −5.50 | 26.50 | 47% |
| 7 | HYMetFMetKMet2FMetD | −4.69 | 26.67 | 42% |

Chromatographic Evaluation of the Peptide Ligands by IgG Binding and Resistance to Proteolytic Enzymes Based on the results reported in Table 2, the original sequences HWRGWV, HFRRHL, and HYFKFD (SEQ ID NOS: 1-3), and their variants HW$_{Met}$CitGW$_{Met}$V, HF$_{Met}$CitCitHL, and HY$_{Met}$F$_{Met}$K$_{(Met)2}$F$_{Met}$D (SEQ ID NOS: 4, 5, 7) were tested for their resistance to enzymatic digestion. The sequences HW$_{Met}$CitGW$_{Met}$V (SEQ ID NO: 8), HF$_{Met}$CitCitHL (SEQ ID NO: 5) were selected as the best variants of their respective original peptides, while HY$_{Met}$F$_{Met}$K$_{Met2}$F$_{Met}$D (SEQ ID NO: 7) was used as a negative control. Finally, two more sequences, HWCitGWV (SEQ ID NO: 10) and HW$_{Met}$RGW$_{Met}$V (SEQ ID NO: 11), were chosen as intermediate variants, hence expected to show resistance to one enzyme only. Each adsorbent was subjected to five consecutive chromatographic runs. First, a solution of pure human polyclonal IgG at 10 mg/mL in PBS was injected to determine IgG yield for each adsorbent prior to contact with any enzyme. All four peptide variants gave a yield above 91% for this initial run. The resin was then contacted with a solution of α-chymotrypsin in Tris buffer pH 8.5 for 10 minutes. The amount of enzyme loaded onto the column was in a mass ratio of 1:100 peptide:enzyme, as done by Verdoliva et al. [35]. After rinsing the resin, a second injection of IgG was then performed to estimate the loss of binding capacity due to the digestion of the peptide ligand by α-chymotrypsin. The resin was then contacted with the second enzyme solution, i.e., trypsin in Tris buffer pH 8.5, at the same peptide:enzyme ratio. A third IgG injection was finally performed to estimate the residual binding capacity of each resin after the second enzyme treatment. FIG. 4 shows the chromatograms of the three IgG injections for the adsorbents HW$_{Met}$CitGW$_{Met}$V-Toyopearl, HW$_{Met}$RGW$_{Met}$V-Toyopearl, HWCitGWV-Toyopearl, and HWRGWV-Toyopearl (SEQ ID NOS: 18, 25, 26, 6) resins.

While HWRGWV (SEQ ID NO: 1) was evidently degraded by both trypsin and α-chymotrypsin, as indicated by the loss of binding capacity after both enzyme treatments (FIG. 2, *a*), its variant $HW_{Met}CitGW_{Met}V$ (SEQ ID NO: 8) is completely unaffected by either (FIG. 2, *d*). As expected, the intermediate variants $HW_{Met}RGW_{Met}V$ (SEQ ID NO: 11) and HWCitGWV (SEQ ID NO: 10) show resistance towards one enzyme only, α-chymotrypsin and trypsin respectively (FIGS. 2, *b* and *c*). The results obtained with the other adsorbents are summarized in Table 3, which reports the values of IgG yield before ($1^{st}$ run) and after treatment with α-chymotrypsin ($2^{nd}$ IgG injection) and trypsin ($3^{rd}$ IgG injection).

FIG. 2 Panels (A)-(D) Show Proteolytic Digests of Natural Peptide Binders and Modified Peptide Binders.

Chromatogram in (A) shows that both proteolytic enzymes digest the original peptide ligand. First, trypsin attacks R, then α-chymotrypsin cleaves at W.

Chromatogram in (B) shows that α-chymotrypsin does not cleave the peptide, owing to the modified $W_M$, while trypsin does cleave the peptide on R.

Chromatogram in (C) shows a similar behavior, whereas trypsin is not ineffective because citrulline replaces R.

Chromatogram in (D) shows no sign of degradation by either enzyme, due to the replacement of W with $W_M$ and of R with citrulline.

Several other peptide sequences have been identified for affinity purification of antibodies from complex media. The sequence APAR (SEQ ID NO: 27) was selected from a synthetic tetrapeptide library for capturing anti-granulocyte macrophage-colony stimulating factor (GM-CSF) monoclonal antibody from mouse ascitic fluid. The peptide ligand PDTRPAP (SEQ ID NO: 28) was identified by epitope mapping with antibodies raised against carcinoma-associated MUC1 mucin. Ehrlich and co-workers isolated the peptide sequence EPIHRSTLTALL (SEQ ID NO: 29) from a phage-display library via biopanning against the pFc fragment of a humanized anti-Tac IgG1 antibody (HAT). Fassina and co-workers identified the tripeptide tetramer $(Arg\text{-}Thr\text{-}Tyr)_4\text{-}Lys_2\text{-}Lys\text{-}Gly$ (SEQ ID NO: 30), also known as TG19318 or PAM (Protein A mimetic), that binds the Fc portion of IgG. Recently, Lund et al. have presented a peptide ligand for IgG purification, called $D_2AAG$ (SEQ ID NO: 31), which comprises arginine (A) and glycine (G) and a synthetic, aromatic acid, 2,6-di-t-butyl-4-hydroxybenzyl acrylate (D). All these peptide ligands known for the purification of antibodies contain either aromatic (tryptophan, phenylalanine, tyrosine) or basic amino acids (lysine and arginine), which makes them prone to proteolytic degradation by trypsin and/or α-chymotrypsin. Therefore the method hereby proposed has a very broad validity for the design of protease-resistant peptide variants. It is therefore possible to build peptide ligand variants which resist to enzymatic cleavage. These ligands can be used for purification of IgG and any other protein of interest from animal plasma.

As an additional note, it should be noted that, being the method herein reported for the production of biochemically stable peptide ligands generally valid for all kinds of target biomolecules to be purified from any desired bodily fluid that may contain proteolytic enzymes, it is possible to automate the process of design of ligand variants and their screening against the target biomolecule. For a given peptide ligand comprising natural amino acid, the software shall create a library of peptide variants using the modified amino acids. This design unit shall also be concatenated with a subsequent docking module, which docks the designed sequences against the target molecule, or, more ideally, to a known binding area on the target molecule. This software package could be of great value for users that do not have facility with professional docking programs.

TABLE 3

Values of IgG yield before and after contacting the resin with enzyme solutions

| SEQ ID NO: | Peptide sequence | IgG Yield $1^{st}$ run | IgG Yield $2^{nd}$ run (after α-chymotrypsin) | IgG Yield $3^{rd}$ run (after trypsin) |
|---|---|---|---|---|
| 1 | HWRGWV | 95% | 72% | 36% |
| 11 | $HW_{Met}RGW_{Met}V$ | 91% | 91% | 82% |
| 10 | HWCitGWV | 91% | 73% | 71% |
| 8 | $HW_{Met}CitGW_{Met}V$ | 90% | 91% | 90% |
| 12 | $HW_{For}CitGW_{For}V$ | 75% | 69% | 69% |
| 3 | HFRRHL | 93% | 78% | 54% |
| 5 | $HF_{Met}CitCitHL$ | 90% | 92% | 91% |
| 2 | HYFKFD | 78% | 76% | 71% |
| 7 | $HY_{Met}F_{Met}K_{(Met)2}F_{Met}D$ | 52% | 49% | 53% |

The results obtained with the ligand HFRRHL (SEQ ID NO: 3) and its derivative $HF_{Met}CitCitHL$ (SEQ ID NO: 5) closely resemble those of HWRGWV (SEQ ID NO: 1) and $HW_{Met}CitGW_{Met}V$ (SEQ ID NO: 8). The sequence HWRGWV (SEQ ID NO: 1) is an ideal substrate for trypsin, most likely because the glycine in the C-position with respect to arginine sterically favors the attack of the enzyme onto the peptide. The peptide HFRRHL (SEQ ID NO: 3) is also a good substrate for trypsin, although the contiguity of the arginines on the sequence slightly reduces the enzymatic attack. HYFKFD (SEQ ID NO: 2), instead, is almost immune to the attack of trypsin, likely due to the steric hindrance of the residues flanking lysine, which can impede the effective anchoring of the enzyme active site on the peptide. Its variant $HY_{Met}F_{Met}K_{(Met)2}F_{Met}D$ (SEQ ID NO: 7) shows high resistance to proteolysis, although the low yield values indicate that the sequence is unfit for protein recovery.

While sequence dependent, these results clearly demonstrate the replacement of natural amino acids with similar synthetic residues, while maintaining similar antibody binding characteristics.

Binding properties as the original sequences, as predicted by the docking simulations, confers high resistance to enzymatic digestion. The methylation of aromatic amino acids significantly reduces the proteolytic attack by α-chymotrypsin, while the use of citrulline and methylated lysine seems to completely prevent the action of trypsin. Despite seeming the most critical of the proposed substitutions, insofar as it reduces the electrostatic component of binding, citrulline proved to be an excellent replacement under both aspects of target binding and biochemical resistance.

Purification of IVIG from Cohn Fraction II+III of Human Plasma Using the Adsorbents $HW_{Met}CitGW_{Met}V$-, $HF_{Met}CitCitHL$, and $HY_{Met}F_{Met}K_{(Met)2}F_{Met}D$-Toyopearl Resin (SEQ ID NOS: 18, 20, 19), To determine the applicability of the proposed ligand variants for IVIG purification, the sequences $HW_{Met}CitGW_{Met}V$ (SEQ ID NO: 8), $HF_{Met}CitCitHL$ (SEQ ID NO: 5), and $HY_{Met}F_{Met}K_{(Met)2}F_{Met}D$ (SEQ ID NO: 7) were used for purifying polyclonal antibodies from Cohn fraction II+III of human plasma. The original peptide ligands were employed as positive controls. The crude stock of Cohn II+III paste was diluted in PBS to prepare the feed sample and solid particles were removed by filtration prior to injection into the column. The chromatographic protocol adopted in this work was derived from previous optimizations and comprised the use of 0.25M NaCl in PBS as binding buffer and 0.2M acetate buffer pH 5.0 for elution [24]. Fractions were collected and analyzed by Protein G chromatography and SDS-PAGE (FIG. 3) to determine IgG yield and purity respectively. A summary of results is presented in Table 4.

TABLE 4

Yields and purity of IgG purified from Cohn fraction II + III of human plasma. IgG purity is determined by densitometric analysis of the Coomassie-stained SDS-PAGE reported in FIG. 3.

| SEQ ID NO: | Sequence | IgG Yield | IgG Purity |
|---|---|---|---|
| 1 | HWRGWV | 85% | 83% |
| 8 | $HW_{Met}CitGW_{Met}V$ | 91% | 92% |
| 3 | HFRRHL | 91% | 86% |
| 5 | $HF_{Met}CitCitHL$ | 89% | 91% |
| 2 | HYFKFD | 54% | 87% |
| 7 | $HY_{Met}F_{Met}K_{(Met)2}F_{Met}D$ | 48% | 90% |
| | Protein A | 94% | 75% |

Product yields and purities obtained with the variants $HW_{Met}CitGW_{Met}V$ (SEQ ID NO: 8) and $HF_{Met}CitCitHL$ (SEQ ID NO: 5) compare well with the results given by the original sequences and Protein A. Although small amounts of albumin can be detected in the eluted fractions (FIG. 3), both ligands offered very high product yield and purity. Most of the observable contaminants simply flow through the column and although some binding of other immunoglobulins, namely IgA and IgM, may occur, the elution conditions (pH 5.0) were chosen to minimize their presence in the eluted fraction [49]. The variant $HY_{Met}F_{Met}K_{(Met)2}F_{Met}D$ (SEQ ID NO: 7) gave high product purity, but performed poorly in terms of yield. While the latter was anticipated based upon the above results, high IgG purity in the eluted fraction was not expected. It is surprising that despite the high sequence hydrophobicity due to the use of alkylated amino acids, there was little non-specific binding of impurities by hydrophobic interaction.

It is also interesting to note that the amount of albumin and other impurities bound by the peptide variants is consistently lower than observed with the original sequences. This can be explained in light of previous findings and the information provided by the docking simulations. The original sequence HWRGWV (SEQ ID NO: 1), for example, which bears two positive charges at pH 7.4, one on arginine and the other on the peptide N-terminus, was found to capture albumin (pI=4.7), the most abundant negatively charged protein present in plasma, by electrostatic interaction. To avoid this non-specific binding of albumin and similar protein impurities, the conductivity of the binding buffer was increased by adding sodium chloride up to an optimum level that gives the best compromise in terms of product yield and purity [25]. The use of salt, however, translates in additional costs to the purification process. The replacement of positively charged residues with electrically neutral amino acids, like citrulline and dimethylated lysine, allows to intrinsically reduce the extent of electrostatic binding regardless of the amount of salt present in the binding buffer. These findings, while explaining the higher purity given by the ligand variants (Table 3), call for a more in depth study on the effect of salt on yields and purity, and this is presented in the section that follows.

Effect of Conductivity on IgG Purification from Cohn Fraction II+III of Human Plasma Using the Adsorbents HWRGWV-Toyopearl, Ac-HWRGWV-Toyopearl, $HW_{Met}CitGW_{Met}V$-Toyopearl, and Ac-$HW_{Met}CitGW_{Met}V$-Toyopearl (SEQ ID NOS: 6, 32, 18, 22) Resins To determine the extent of the electrostatic component of binding, the effect of conductivity of the binding buffer on product yield and purity was studied using four peptide ligands with different charge value and distribution: a) the original HWRGWV (SEQ ID NO: 1), b) its acetylated version Ac-HWRGWV (SEQ ID NO: 32), c) the variant $HW_{Met}CitGW_{Met}V$ (SEQ ID NO: 8), and d) its acetylated version Ac-$HW_{Met}CitGW_{Met}V$ (SEQ ID NO: 9).

The four sequences were used for purifying IVIG from Cohn fraction II+III. As mentioned above, in previous studies of IVIG purification using HWRGWV (SEQ ID NO: 1), PBS+0.25M NaCl was chosen as the optimal binding buffer. The results obtained in the previous section led to the hypothesis that the replacement of positively charged amino acids with neutral residues would reduce the electrostatic behavior of the ligands and hence increase product purity. To verify this hypothesis, binding studies were repeated using the above listed sequences and three binding buffers, comprising 0M, 0.13M, and 0.25M NaCl in PBS. FIG. 4 shows the SDS-PAGE results obtained at different conductivities with each of the four adsorbents, while Table 9 reports the resulting values of product yield and purity. FIG. 3. SDS-PAGE (reducing conditions) of chromatographic purification of IgG from Cohn fraction II+III of human plasma using the adsorbents: a) HWRGWV-Toyopearl (SEQ ID NO: 6) resin and $HW_{Met}CitGW_{Met}V$-Toyopearl resin (SEQ ID NO: 18); b) HFRRHL-Toyopearl (SEQ ID NO: 17) resin and $HF_{Met}CitCitHL$-Toyopearl (SEQ ID NO: 20) resin; and c) HYFKFD-Toyopearl resin (SEQ ID NO: 16) and $HY_{Met}F_{Met}K_{(Met)2}F_{Met}D$-Toyopearl (SEQ ID NO: 19) resin. Labels: FT—flow-through fraction; EL—elution fraction.

FIG. 4. SDS-PAGE (reducing conditions) of chromatographic purification of IgG from Cohn fraction II+III of human plasma performed at different salt concentration in the binding buffer: a) HWRGWV (SEQ ID NO: 1) and Ac-HWRGWV (SEQ ID NO: 32), b) $HW_{Met}CitGW_{Met}V$ (SEQ ID NO: 8) and Ac-$HW_{Met}CitGW_{Met}V$ (SEQ ID NO: 9). Labels: FT flow-through fraction; EL elution fraction.

TABLE 5

Yields and purity of IgG purified from Cohn fraction II + III of human plasma using binding buffers at different salt concentration. IgG purity is determined by densitometric analysis of the Coomassie-stained SDS-PAGE reported in FIG. 4.

| SEQ | | 0M NaCl | | 0.13M NaCl | | 0.25M NaCl | |
|---|---|---|---|---|---|---|---|
| ID NO: | Sequence | IgG Yield | IgG Purity | IgG Yield | IgG Purity | IgG Yield | IgG Purity |
| 1 | HWRGWV | 90% | 81% | 85% | 83% | 85% | 83% |
| 32 | Ac-HWRGWV | 91% | 80% | 84% | 80% | 83% | 84% |
| 8 | $HW_{Met}CitGW_{Met}V$ | 89% | 91% | 90% | 91% | 91% | 92% |
| 9 | Ac-$HW_{Met}CitGW_{Met}V$ | 91% | 93% | 93% | 90% | 94% | 92% |

As Table 5 indicates, lowering the number of positive charges on the peptide leads to higher IgG purity. As expected, the effect of conductivity of the binding buffer on product purity is very evident for HWRGWV (SEQ ID NO: 1), which bears two positive charges and is hence the most susceptible to the shielding of electrostatic forces, while the effect of conductivity is nearly negligible for Ac-$HW_{Met}CitGW_{Met}V$ (SEQ ID NO: 9). A comparison between the latter and $HW_{Met}CitGW_{Met}V$ (SEQ ID NO: 8), as well as the original sequence and its acetylated form, show that the acetylation of the peptide N-terminus is less influential on product yield and purity than the replacement of arginine with citrulline. The IgG purity (93%) obtained with Ac-$HW_{Met}CitGW_{Met}V$ (SEQ ID NO: 9) using a low conductivity binding buffer is higher than any value obtained using HWRGWV (SEQ ID NO: 1) (81%-83%). Notably, high purity has not been achieved at the expense of yield, which remained stably above 90%, even though some decrease was expected based upon the results of the docking calculations, which predicted for the variant a $\Delta_i G$ of binding slightly lower than that of the original sequence. The sequence Ac-$HW_{Met}CitGW_{Met}V$ (SEQ ID NO: 9) possesses many required features for an affordable and robust process of antibody purification based on small peptide ligand affinity chromatography.

CONCLUSION

This study offers a strategy for the design of small peptide ligands comprising non-natural amino acids with excellent characteristics of target affinity and selectivity, and biochemical stability. Based on the information available for known peptide sequences, in particular the binding site on the target biomolecule, and the use of state-of-the-art modeling tools, this method directs the replacement of key amino acid residues with non-natural variants to conveniently modify the binding mechanism or to confer stability against chemical and biological agents, such as strong acids and bases, and proteolytic enzymes. Three antibody binding peptides, HWRGWV (SEQ ID NO: 1), HYFKFD (SEQ ID NO: 2), and HFRRHL (SEQ ID NO: 3), were utilized as models to develop ligand variants that show higher proteolytic resistance and maintain high target affinity and specificity. Due to the high value of antibodies recovered from plasma-based fluids, like Cohn fractions and hybridoma cell culture, this work aimed to confer the peptides with biochemical stability against the major plasma proteases, trypsin and α-chymotrypsin. To this end, a virtual library of variants was designed by replacing aromatic and basic amino acids with methylated variants and citrulline, and then screened in-silico against the peptide binding site on IgG (Ser383-Asn389) using the molecular docking software HADDOCK.

The peptide variants selected based on the results of docking calculations were synthesized on chromatographic resins and tested for resistance to proteolysis and purification of IVIG from Cohn fraction II+III of human plasma. These variants possess target affinity comparable to their parental sequences and a much higher biochemical resistance. Furthermore, an in-depth study on the electrostatic component of the IgG binding mechanism of HWRGWV-related variants resulted in the identification of the sequence Ac-$HW_{Met}CitGW_{Met}V$ (SEQ ID NO: 9), which exhibits higher selectivity than the original HWRGWV (SEQ ID NO: 1). The adsorbent Ac-$HW_{Met}CitGW_{Met}V$-Toyopearl (SEQ ID NO: 22) resin demonstrated intrinsically lower binding of albumin and other impurities, which translates into lower amount of salt needed in the binding buffer to attain high IgG purity and hence lower purification costs.

The approach used here is generally valid for any small synthetic or natural peptide ligand targeting a biomolecule. Once the binding site is known with good approximation, it is possible to design and screen large libraries, quickly and inexpensively using reliable programs for molecular docking. These tools, in addition to providing good estimations of the binding strength, also offer insights regarding the nature of ligand-target interactions. The judicious choice of amino acid substitutions enables fine-tuning of the biochemical properties of the peptide ligands. In particular, by modifying the distribution of charge as well as hydrophobic and hydrophilic groups, it is possible to enhance, affinity and selectivity in addition to biochemical stability. The use of synthetic variants in place of amino acids that are prone to chemical degradation, e.g., asparagine and glutamine which undergo deamidation in alkaline conditions, is particularly suited for designing peptide ligands for affinity chromatography, where harsh chemical agents are used for protein elution and column cleaning and sanitization. Reducing the extent of chemical degradation translates into longer adsorbent lifetime.

The approach presented herein is also amenable for fundamental studies of the non-covalent interactions that underlie the mechanisms of protein activity. By silencing or activating specific components of binding using suitable amino acids, it is possible to study the phenomena of biorecognition and design small biomolecules that control the specific interactions between target and ligand. This work offers an example in this direction by presenting small peptide variants that, in several respects, outperform Protein A in binding target antibodies. These findings represent a further step towards optimal synthetic protein mimetics with great potential for bioseparations and, more generally, a variety of applications in biotechnology.

REFERENCES

[1] O. H. Brekke, I. Sandlie, Nat. Rev. Drug Discovery 2 (2003) 52.

[2] C. Newcombe, A. R. Newcombe, J. Chromatogr. B 848 (2007) 2.

[3] A. ElBakri, P. N. Nelson, A. O. R. O. A., Hum. Immunol 71 (2010) 1243.

[4] N. Ronda, V. Hurez, M. D. Kazatchkine, Vox Sang. 64 (1993) 65.

[5] M. D. Kazatchkine, S. V. Kaveri, N. Engl. J. Med. 345 (2001) 747.

[6] U. Jeschke, A. Bischof, R. Speer, V. Briese, D. U. Richter, C. Bergemann, I. Mylonas, N. Shabani, K. Friese, U. Karsten, Anticancer Res. 25 (2005) 1581.

[7] N. Lonberg, Nat. Biotechnol. 23 (2005) 1117.

[8] J. W. Stave, Food Control 10 (1999) 367.

[9] H. Zola, eLS (2005).

[10] C. Zhang, in G. Proetzel, H. Ebersbach (Editors), Antibody methods and protocols, Humana Press, 2012, p. 117.

[11] M. P. Backer, L. S. Metzger, P. L. Slaber, K. L. Nevin, G. B. Boder, Biotechnol. Bioeng. 32 (1988) 993.

[12] A. C. Grodzki, E. Berenstein, Methods Mol. Biol. 588 (2010) 33.

[13] R. Hahn, R. Schlegel, A. Jungbauer, J. Chromatogr. B Analyt. Technol. Biomed. Life Sci. 790 (2003) 35.

[14] D. K. Follman, R. L. Fahrner, J. Chromatogr. A 1024 (2004) 79.

[15] S. Hober, K. Nord, M. Linhult, J. Chromatogr. B 848 (2007) 40.

[16] G. E. Healthcare, in D. F. -. -. A A (Editor), 2005.

[17] P. A. Nygren, M. Eliasson, L. Abrahmsen, M. Uhlen, E. Palmcrantz, J. Mol. Recognit. 1 (1988) 69.

[18] M. Page, R. Thorpe, in J. M. Walker (Editor), The protein protocols handbook, Humana Press, 1996, p. 733.

[19] P. Gagnon, J. Chromatogr. A 1221 (2012) 57.

[20] B. Vijayalakshmi Ayyar, S. Arora, C. Murphy, R. O'Kennedy, Methods 56 (2012) 116.

[21] H. Yang, P. V. Gurgel, R. G. Carbonell, J. Pept. Res. 66 Suppl (2005) 120.

[22] H. Yang, P. V. Gurgel, R. G. Carbonell, J. Chromatogr. A 1216 (2009) 910.
[23] H. G. Yang, P. V. Gurgel, D. K. Williams, B. G. Bobay, J. Cavanagh, D. C. Muddiman, R. G. Carbonell, J. Mol. Recognit. 23 (2010) 271.
[24] S. Menegatti, A. D. Naik, P. V. Gurgel, R. G. Carbonell, J. Pept. Sci (2012).
[25] A. D. Naik, S. Menegatti, P. V. Gurgel, R. G. Carbonell, J. Chromatogr. A 1218 (2011) 1691.
[26] A. D. Naik, S. Menegatti, H. R. Reese, P. V. Gurgel, R. G. Carbonell, J. Chromatogr. A (2012).
[27] W. S. Kish, A. D. Naik, S. Menegatti, R. G. Carbonell, Ind. Eng. Chem. Res. (2012).
[28] S. Menegatti, A. D. Naik, P. V. Gurgel, R. G. Carbonell, J. Chromatogr. A 1245 (2012) 55.
[29] J. M. Artigas, M. E. Garcia, M. R. Faure, A. M. Gimeno, Postgrad. Med. J. 57 (1981) 219.
[30] R. B. Llfkowitz, J. Y. Marciniak, Electrophoresis 31 (2010) 403.
[31] J. V. Olsen, S. E. Ong, M. Mann, Mol. Cell. Proteomics 3 (2004) 608.
[32] W. Appel, Clin. Biochem. 19 (1986) 317.
[33] R. L. Fahrner, A. Laverdiere, P. J. McDonald, R. M. O'Leary, in U. P. Office (Editor), United States, 2010.
[34] B. D'Agostino, P. Bellofiore, T. De Martino, C. Punzo, V. Rivieccio, A. Verdoliva, J. Immunol. Methods 333 (2008) 126.
[35] A. Verdoliva, F. Pannone, M. Rossi, S. Catello, V. Manfredi, J. Immunol. Methods 271 (2002) 77.
[36] R. Bischoff, H. V. Kolbe, J. Chromatogr. B Biomed. Appl. 662 (1994) 261.
[37] A. B. Joshi, L. E. Kirsch, J. Pharm. Sci. 91 (2002) 2331.
[38] K. L. Schey, E. L. Finley, Acc. Chem. Res. 33 (2000) 299.
[39] T. J. Simat, H. Steinhart, J. Agric. Food Chem. 46 (1998) 490.
[40] S. J. de Vries, A. D. J. van Djik, M. Krzeminski, M. van Dijk, A. Thureau, V. Hsu, T. Wassenaar, A. M. Bonvin, Proteins: Struc. Funct. & Bioinformatic 69 (2007) 726.
[41] C. Dominguez, R. Boelens, A. M. Bonvin, J. Am. Chem. Soc. 125 (2003) 1731.
[42] R. Wang, Y. Lu, S. Wang, J. Med. Chem. 46 (2003) 2287.
[43] N. Andrusier, E. Maschiach, R. Nussinov, H. J. Wolfson, Proteins 73 (2008) 271.
[44] E. Maschiach, D. Schneidman-Duhovny, N. Andrusier, R. Nussinov, H. J. Wolfson, Nucleic Acids Res. 36 (2008) W229.
[45] S. Liu, C. Zhang, H. Zhou, Y. Zhou, Proteins 56 (2004) 93.
[46] A. E. Sauer-Eriksson, G. Kleywegt, M. Uhlen, T. A. Jones, Structure 3 (1995) 265.
[47] R. Wang, L. Lai, S. Wang, J. Comput. Aided Mol. Des. 16 (2002) 11.
[48] S. J. Hubbard, S. F. Campbell, J. M. Thornton, J. Mol. Biol. 220 (1991) 507.
[49] Z. Liu, P. V. Gurgel, R. G. Carbonell, J. Chromatogr. A 1262 (2012) 169.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application was specifically and individually indicated to be incorporated by reference.

TABLE 6

| non-natural amino acid examples | | | | |
|---|---|---|---|---|
| Glutamine | N-γ-ethyl-glutamine | | | |
| Glutamic acid | carboxy-glutamic acid | | | |
| Proline | 3-hydroxy-proline | 4-hydroxy-proline | 5-hydroxy-proline | |
| | 3-phenyl-proline | 4-phenyl-proline | 5-phenyl-proline | |
| | 3-benzyl-proline | 4-benzyl-proline | 5-benzyl-proline | |
| Phenylalanine | carbamoyl-phenylalanine | 4-amino-phenylalanine | 5-amino-phenylalanine | 6-amino-phenylalanine |
| | diphenylalanine | 4-aminomethyl-phenylalanine | 5-aminomethyl-phenylalanine | 6-aminomethyl-phenylalanine |
| Tyrosine | methyl-tyrosine | 2-methoxy-phenylalanine | 3-methoxy-phenylalanine | 3,4-hydroxy-phenylalanine |
| | ethyl-tyrosine | 2-ethoxy-phenylalanine | 3-ethoxy-phenylalanine | 3,4-methoxy-phenylalanine |
| | 3-amino-tyrosine | aminoethoxy-phenylalanine | thyronine | 2,4,5-trihydroxy-phenylalanine |
| Arginine | methyl-arginine | methyl-arginine | N,N'-dimethyl-arginine | N,N-dimethyl-arginine |
| | Citrulline | canavanine | nitro-arginine | |
| Lysine | methyl-lysine | dimethyl-lysine | | |
| Serine | methyl-serine | benzyl-serine | | |
| Threonine | methyl-threonine | benzyl-threonine | | |
| Histidine | methyl-histidine | histidine | methyl-histidine | |
| Tryptophan | 5-hydroxy-tryptophan | 1-methyl-tryptophan | 1-formyl-tryptophan | 5-methyoxy-tryptophan |
| | 7-aza-tryptophan | | | |
| 2-pyridyl-alanine | 3-pyridyl-alanine | 4-pyridyl-alanine | 1-naphtyl-alanine | 2-naphtyl-alanine |
| 2-thienyl-alanine | 2-benzothienyl-alanine | t-butyl-alanine | 2-indanyl-alanine | |

What is claimed is:

1. A peptide capable of binding a biological, the peptide comprising:

one or more hexapeptides selected from the group consisting of HWRGWV (SEQ ID NO:1), HYFKFD (SEQ ID NO:2) and HFRRHL (SEQ ID NO:3);

wherein the HWRGWV (SEQ ID NO:1) hexapeptide is selected from the group consisting of $HW_{Met}CitGW_{Met}V$ (SEQ ID NO:4), HWCitGWV (SEQ ID NO:10), $HW_{met}CitGW_{met}V$ (SEQ ID NO:8), and $HW_{met}RGW_{met}V$ (SEQ ID NO:11), wherein the HYFKFD (SEQ ID NO:2) hexapeptide is selected from the group consisting of $HY_{for}CitGW_{for}V$ (SEQ ID NO:12), $HY_{met}F_{met}K_{met}F_{met}D$ (SEQ ID NO:13), and $HY_{met}F_{met}K_{met}2F_{met}D$ (SEQ ID NO:7), wherein the HFRRHL (SEQ ID NO:3) hexapeptide is selected from the group consisting of $HF_{met}CitCitHL$ (SEQ ID NO:5) and $HF_{carb}CitCitHL$ (SEQ ID NO:14), wherein the one or more hexapeptides comprise at least one non-natural amino acid selected from the group consisting of $N_{in}$-methyl-tryptophan, $N_{in}$-formyl-tryptophan, 4-methylphenylalanine, 4-carbamoyl-phenylalanine, O-methyl-tyrosine, e-dimethyl-lysine, and citrulline; and wherein the peptide is resistant to digestion by a protease.

2. The protease-resistant peptide of claim 1, wherein the peptide is resistant to digestion by endopeptidases.

3. The protease-resistant peptide of claim 1, wherein the peptide is resistant to digestion by exopeptidases.

4. The protease-resistant peptide of claim 2, wherein the endopeptidase is alpha-chymotrypsin.

5. The protease-resistant peptide of claim 2, wherein the endopeptidase is trypsin.

6. A chromatographic material comprising a solid support, wherein the solid support is coupled to any of the protease-resistant peptides of claim 1.

7. The protease-resistant peptide of claim 1, wherein the biological is an antibody that comprises an IgG domain.

8. The chromatographic material of claim 6, wherein the solid support comprises resin beads.

9. The chromatographic material of claim 8, wherein the resin beads comprise amino activated polymethacrylate.

10. A method for isolating a biological, the method comprising:

contacting a chromatographic material with a biological-containing preparation under binding conditions in which the biological is capable of binding to a protease-resistant peptide, wherein the protease-resistant peptide comprises one or more hexapeptides selected from the group consisting of HWRGWV (SEQ ID NO:1), HYFKFD (SEQ ID NO:2) and HFRRHL (SEQ ID NO:3), wherein the HWRGWV (SEQ ID NO:1) hexapeptide is selected from the group consisting of $HW_{Met}CitGW_{Met}V$ (SEQ ID NO:4), HWCitGWV (SEQ ID NO:10), $HW_{met}CitGW_{met}V$ (SEQ ID NO:8), and $HW_{met}RGW_{met}V$ (SEQ ID NO:11), wherein the HYFKFD (SEQ ID NO:2) hexapeptide is selected from the group consisting of $HY_{for}CitGW_{for}V$ (SEQ ID NO:12), $HY_{met}F_{met}K_{met}F_{met}D$ (SEQ ID NO:13), and $HY_{met}F_{met}K_{met}2F_{met}D$ (SEQ ID NO:7), wherein the HFRRHL (SEQ ID NO:3) hexapeptide is selected from the group consisting of $HF_{met}CitCitHL$ (SEQ ID NO:5) and $HF_{carb}CitCitHL$ (SEQ ID NO:14), and wherein the one or more hexapeptides comprise at least one non-natural amino acid selected from the group consisting of Nin-methyl-tryptophan, Nin-formyl-tryptophan, 4-methylphenylalanine, 4-carbamoyl-phenylalanine, O-methyl-tyrosine, e-dimethyl-lysine, and citrulline;

washing the chromatographic material and the bound biological; and eluting the biological from the chromatographic material so as to isolate the biological.

11. The method of claim 10, wherein the biological compound is an antibody that comprises an IgG domain.

12. A diagnostic kit for detecting the presence of a biological comprising the chromatographic material of claim 6, wherein the biological is an antibody that comprises an IgG domain.

* * * * *

SEQUENCE LISTING

<160> NUMBER OF SEQ ID NOS: 32

<210> SEQ ID NO 1
<211> LENGTH: 6
<212> TYPE: PRT
<213> ORGANISM: Artificial
<220> FEATURE:
<223> OTHER INFORMATION: Synthetic

<400> SEQUENCE: 1

His Trp Arg Gly Trp Val
1 5

<210> SEQ ID NO 2
<211> LENGTH: 6
<212> TYPE: PRT
<213> ORGANISM: Artificial
<220> FEATURE:
<223> OTHER INFORMATION: synthetic

<400> SEQUENCE: 2

His Tyr Phe Lys Phe Asp
1 5

<210> SEQ ID NO 3
<211> LENGTH: 6
<212> TYPE: PRT
<213> ORGANISM: Artificial
<220> FEATURE:
<223> OTHER INFORMATION: Synthetic

<400> SEQUENCE: 3

His Phe Arg Arg His Leu
1 5

<210> SEQ ID NO 4
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: METHYLATION

<400> SEQUENCE: 4

His Trp Xaa Gly Trp Val
1 5

<210> SEQ ID NO 5
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (4)..(4)
<223> OTHER INFORMATION: CITRULLINE

<400> SEQUENCE: 5

His Phe Xaa Xaa His Leu
1 5

<210> SEQ ID NO 6
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: TOYOPEARL

<400> SEQUENCE: 6

His Trp Arg Gly Trp Val
1 5

<210> SEQ ID NO 7
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: DIMETHYLATION

<400> SEQUENCE: 7

His Tyr Phe Lys Phe Asp
1 5

<210> SEQ ID NO 8
<211> LENGTH: 6
<212> TYPE: PRT
<213> ORGANISM: artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (5)..(5)
<223> OTHER INFORMATION: METHYLATION

<400> SEQUENCE: 8

His Trp Xaa Gly Trp Val
1 5

-continued

<210> SEQ ID NO 9
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (5)..(5)
<223> OTHER INFORMATION: METHYLATION

<400> SEQUENCE: 9

His Trp Xaa Gly Trp Val
1               5

<210> SEQ ID NO 10
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: CITRULLINE

<400> SEQUENCE: 10

His Trp Xaa Gly Trp Val
1               5

<210> SEQ ID NO 11
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: METHYLATION

<400> SEQUENCE: 11

His Trp Arg Gly Trp Val
1               5

<210> SEQ ID NO 12
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: FORMYLATION
<220> FEATURE:

<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (5)..(5)
<223> OTHER INFORMATION: FORMYLATION

<400> SEQUENCE: 12

His Trp Xaa Gly Trp Val
1 5

<210> SEQ ID NO 13
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (5)..(5)
<223> OTHER INFORMATION: METHYLATION

<400> SEQUENCE: 13

His Tyr Phe Lys Phe Asp
1 5

<210> SEQ ID NO 14
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: CARBOXYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (4)..(4)
<223> OTHER INFORMATION: CITRULLINE

<400> SEQUENCE: 14

His Phe Xaa Xaa His Leu
1 5

<210> SEQ ID NO 15
<211> LENGTH: 7
<212> TYPE: PRT
<213> ORGANISM: Artificial
<220> FEATURE:
<223> OTHER INFORMATION: Synthetic

<400> SEQUENCE: 15

Ser Asn Gly Gln Pro Glu Asn
1 5

<210> SEQ ID NO 16
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: TOYOPEARL

<400> SEQUENCE: 16

His Tyr Phe Lys Phe Asp
1               5

<210> SEQ ID NO 17
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: TOYOPEARL

<400> SEQUENCE: 17

His Phe Arg Arg His Leu
1               5

<210> SEQ ID NO 18
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: TOYOPEARL

<400> SEQUENCE: 18

His Trp Xaa Gly Trp Val
1               5

<210> SEQ ID NO 19
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: DIMETHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: TOYOPEARL

<400> SEQUENCE: 19

His Tyr Phe Lys Phe Asp
1               5

<210> SEQ ID NO 20
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (4)..(4)
<223> OTHER INFORMATION: CITRULLINE
<220> FEATURE:
<221> NAME/KEY: MOD_RES
<222> LOCATION: (6)..(6)
<223> OTHER INFORMATION: TOYOPEARL

<400> SEQUENCE: 20

His Phe Xaa Xaa His Leu
1               5

<210> SEQ ID NO 21
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: TOYOPEARL

<400> SEQUENCE: 21

His Trp Arg Gly Trp Val
1               5

<210> SEQ ID NO 22
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: TOYOPEARL

<400> SEQUENCE: 22

His Trp Xaa Gly Trp Val
1               5

<210> SEQ ID NO 23
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (4)..(4)
<223> OTHER INFORMATION: CITRULLINE

<400> SEQUENCE: 23

His Phe Xaa Xaa His Leu
1               5

<210> SEQ ID NO 24
<211> LENGTH: 4
<212> TYPE: PRT
<213> ORGANISM: Artificial
<220> FEATURE:
<223> OTHER INFORMATION: Synthetic

<400> SEQUENCE: 24

Ser Asn Gly Gln
1

<210> SEQ ID NO 25
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (6)..(6)
<223> OTHER INFORMATION: TOYOPEARL

<400> SEQUENCE: 25

His Trp Arg Gly Trp Val
1 5

<210> SEQ ID NO 26
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: CITRULLINE
<220> FEATURE:
<221> NAME/KEY: MOD_RES
<222> LOCATION: (6)..(6)
<223> OTHER INFORMATION: TOYOPEARL

<400> SEQUENCE: 26

His Trp Xaa Gly Trp Val
1 5

<210> SEQ ID NO 27
<211> LENGTH: 4
<212> TYPE: PRT
<213> ORGANISM: Artificial
<220> FEATURE:
<223> OTHER INFORMATION: Synthetic

<400> SEQUENCE: 27

Ala Pro Ala Arg
1

<210> SEQ ID NO 28
<211> LENGTH: 7
<212> TYPE: PRT
<213> ORGANISM: Artificial
<220> FEATURE:
<223> OTHER INFORMATION: Synthetic

<400> SEQUENCE: 28

Pro Asp Thr Arg Pro Ala Pro
1 5

<210> SEQ ID NO 29
<211> LENGTH: 12
<212> TYPE: PRT
<213> ORGANISM: Artificial
<220> FEATURE:
<223> OTHER INFORMATION: Synthetic

<400> SEQUENCE: 29

Glu Pro Ile His Arg Ser Thr Leu Thr Ala Leu Leu
1 5 10

<210> SEQ ID NO 30
<211> LENGTH: 16
<212> TYPE: PRT
<213> ORGANISM: Artificial
<220> FEATURE:
<223> OTHER INFORMATION: Synthetic

<400> SEQUENCE: 30

Arg Thr Tyr Arg Thr Tyr Arg Thr Tyr Arg Thr Tyr Lys Lys Lys Gly
1 5 10 15

-continued

```
<210> SEQ ID NO 31
<211> LENGTH: 5
<212> TYPE: PRT
<213> ORGANISM: Artificial
<220> FEATURE:
<223> OTHER INFORMATION: Synthetic

<400> SEQUENCE: 31

Asp Asp Ala Ala Gly
1               5


<210> SEQ ID NO 32
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: TOYOPEARL

<400> SEQUENCE: 32

His Trp Arg Gly Trp Val
1               5
```